(12) United States Patent
Nagae

(10) Patent No.: US 10,788,676 B2
(45) Date of Patent: Sep. 29, 2020

(54) BRANCHING OPTICAL SYSTEM, IMAGING APPARATUS, AND IMAGING SYSTEM

(71) Applicant: Sony Corporation, Tokyo (JP)

(72) Inventor: Satoshi Nagae, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/461,794

(22) PCT Filed: Oct. 17, 2017

(86) PCT No.: PCT/JP2017/037452
§ 371 (c)(1),
(2) Date: May 17, 2019

(87) PCT Pub. No.: WO2018/131240
PCT Pub. Date: Jul. 19, 2018

(65) Prior Publication Data
US 2019/0361252 A1    Nov. 28, 2019

(30) Foreign Application Priority Data

Jan. 16, 2017    (JP) ................................. 2017-005249

(51) Int. Cl.
*G02B 27/12* (2006.01)
*A61B 1/00* (2006.01)
(Continued)

(52) U.S. Cl.
CPC ........ *G02B 27/126* (2013.01); *A61B 1/00096* (2013.01); *G02B 21/361* (2013.01);
(Continued)

(58) Field of Classification Search
None
See application file for complete search history.

(56) References Cited

U.S. PATENT DOCUMENTS

| 7,531,781 B2 * | 5/2009 | Sumi | G02B 5/282 |
| | | | 250/208.1 |
| 9,229,238 B2 * | 1/2016 | Higashiyama | H04N 9/09 |

(Continued)

FOREIGN PATENT DOCUMENTS

| JP | 05-341110 | * 12/1993 | ............... G02B 5/04 |
| JP | 5-341110 A | 12/1993 | |

(Continued)

OTHER PUBLICATIONS

International Search Report and Written Opinion dated Dec. 26, 2017 for PCT/JP2017/037452 filed on Oct. 17, 2017, 10 pages including Translation of the International Search Report.

*Primary Examiner* — Reza Aghevli
(74) *Attorney, Agent, or Firm* — Xsensus LLP

(57) ABSTRACT

[Object] In a configuration in which an image of a target is captured using a plurality of imaging elements, the plurality of imaging elements can be efficiently disposed in a limited space.
[Solving Means] A branching optical system includes: a first branching optical system that separates first light belonging to a predetermined wavelength band from incident light in a first direction that is a surface direction of a plane including an optical axis corresponding to a normal direction of an incidence surface on which the incident light is incident; and a second branching optical system that is provided subsequent to the first branching optical system and separates, from second light after the first light is separated from the incident light, third light that is a part of the second light, in a second direction crossing the plane.

19 Claims, 14 Drawing Sheets

(51) Int. Cl.
  *G02B 21/36* (2006.01)
  *H04N 9/097* (2006.01)
  *H04N 13/243* (2018.01)
  *H04N 5/225* (2006.01)
(52) U.S. Cl.
  CPC ........... *H04N 5/2258* (2013.01); *H04N 9/097* (2013.01); *H04N 13/243* (2018.05); *H04N 2005/2255* (2013.01)

(56) References Cited

U.S. PATENT DOCUMENTS

| | | | | |
|---|---|---|---|---|
| 2014/0285702 A1* | 9/2014 | Higashiyama | ...... | G02B 27/1013 |
| | | | | 348/336 |
| 2015/0182118 A1* | 7/2015 | Bradbury | ............ | A61B 1/0005 |
| | | | | 600/431 |
| 2016/0178917 A1* | 6/2016 | Saita | ........................ | G02B 5/04 |
| | | | | 348/336 |
| 2017/0038572 A1* | 2/2017 | Mori | ................... | G02B 21/0076 |
| 2017/0219834 A1* | 8/2017 | Horiguchi | ................ | H04N 9/09 |
| 2017/0261368 A1* | 9/2017 | Nam | .................. | H01L 31/02162 |
| 2017/0289467 A1* | 10/2017 | Yamamoto | ........... | A61B 1/0646 |
| 2018/0045500 A1* | 2/2018 | Chen | .................. | G01B 9/02075 |
| 2018/0131917 A1* | 5/2018 | Sato | ...................... | G02B 27/283 |
| 2018/0180886 A1* | 6/2018 | Holland | ................. | H04N 9/3129 |
| 2019/0101760 A1* | 4/2019 | Ayres | ................. | G02B 27/0172 |
| 2019/0170647 A1* | 6/2019 | Ikenaga | .................. | A61B 90/37 |
| 2019/0179063 A1* | 6/2019 | Ayres | ........................ | G03H 1/28 |
| 2019/0234875 A1* | 8/2019 | Yasuura | ............... | G01N 21/645 |
| 2019/0283179 A1* | 9/2019 | Kakizaki | .............. | B23K 26/142 |

FOREIGN PATENT DOCUMENTS

| | | |
|---|---|---|
| JP | 2016-178995 A | 10/2016 |
| WO | 2013/084434 A1 | 6/2013 |

\* cited by examiner

FIG.11
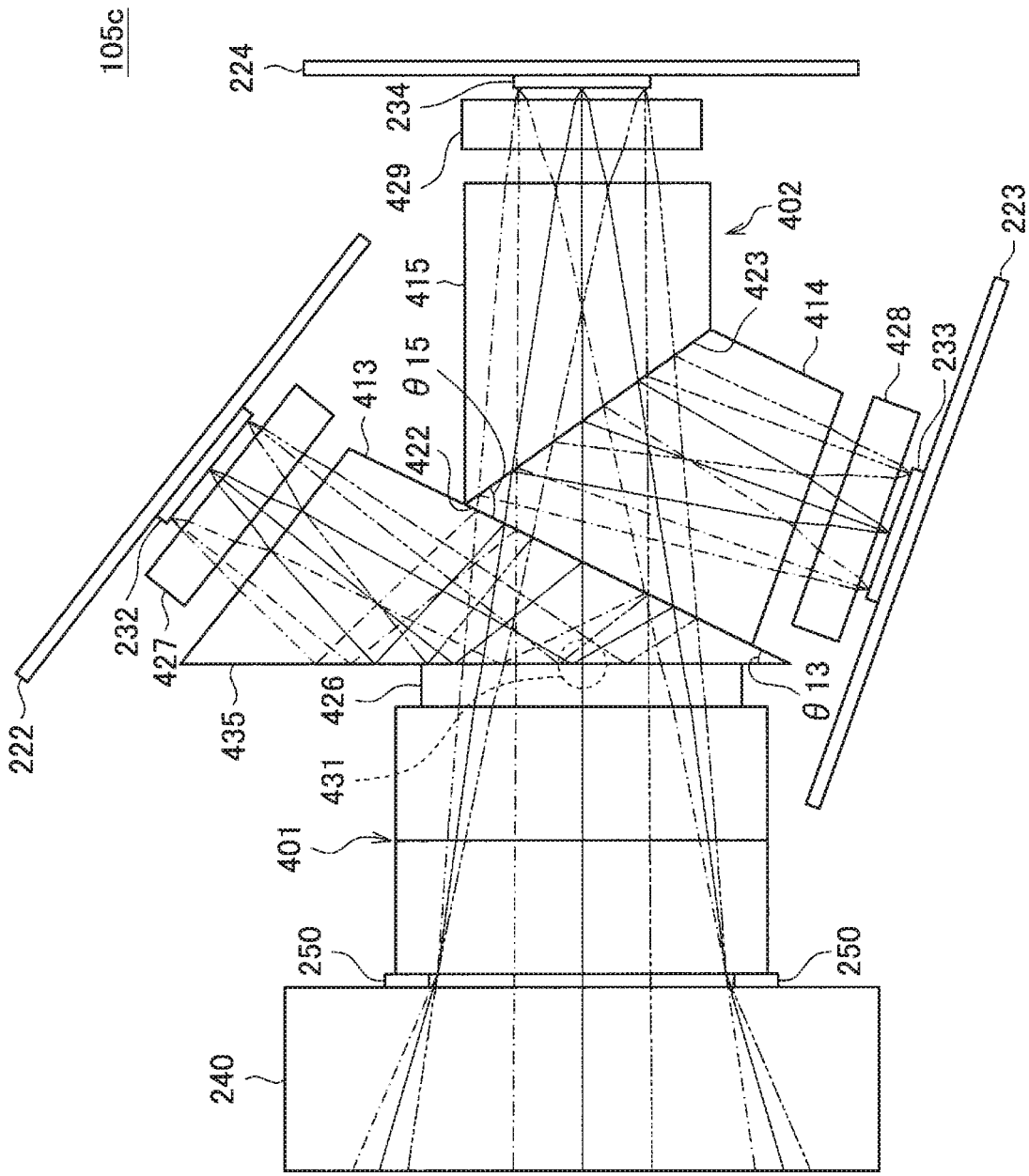
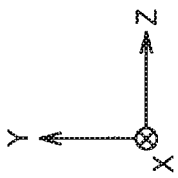

BRANCHING OPTICAL SYSTEM, IMAGING APPARATUS, AND IMAGING SYSTEM

CROSS-REFERENCE TO RELATED APPLICATIONS

The present application is based on PCT filing PCT/JP2017/037452 filed Oct. 17, 2017 which claims priority to JP 2017-005249 filed Jan. 16, 2017, the entire contents of each are incorporated herein by reference.

TECHNICAL FIELD

The present technology relates to a branching optical system, an imaging apparatus, and an imaging system.

BACKGROUND ART

In recent years, with an improvement in performance or miniaturization of imaging apparatuses, such as so-called digital cameras, the use of such imaging apparatuses has also been diversified. For example, in the medical field, a so-called medical observation apparatus has been proposed that presents an electronic image of an affected part to a user (for example, a doctor) through a display device, such as a monitor, by making an imaging apparatus capture an image of the affected part acquired by an optical system unit, such as an endoscope or a surgical microscope.

In particular, in the medical field, an imaging apparatus or an imaging system capable of capturing an image with further improved color reproducibility or resolution has been required, and various imaging apparatuses or imaging systems corresponding to such requirements have also been proposed. For example, Patent Literature 1 discloses an example of an endoscope system capable of further improving the image quality of a captured image by separating light from a target into a plurality of spectral components using a so-called color separation optical system and focusing the plurality of separated spectral components on different imaging elements.

CITATION LIST

Patent Literature

Patent Literature 1: Japanese Patent Application Laid-open No. 2016-178995

SUMMARY OF INVENTION

Technical Problem

On the other hand, in an imaging apparatus using a color separation optical system, a plurality of imaging elements for imaging respective spectral components separated by the color separation optical system needs to be disposed in a limited space without interfering with each other. For this reason, as the number of imaging elements to be disposed increases, the space for disposing the color separation optical system or the imaging elements is more limited. Further, in the medical field, there is a demand for miniaturization of various medical devices so as not to obstruct medical practice, and imaging apparatuses are no exception. That is, as the imaging apparatus becomes smaller, the space for disposing the color separation optical system or the imaging elements is further limited.

Therefore, in the present disclosure, a branching optical system, an imaging apparatus, and an imaging system will be proposed in which a plurality of imaging elements can be efficiently disposed in a limited space in a configuration in which an image of a target is captured using the plurality of imaging elements.

Solution to Problem

In accordance with the present disclosure, there is provided a branching optical system including: a first branching optical system that separates first light belonging to a predetermined wavelength band from incident light in a first direction that is a surface direction of a plane including an optical axis corresponding to a normal direction of an incidence surface on which the incident light is incident; and a second branching optical system that is provided subsequent to the first branching optical system and separates, from second light after the first light is separated from the incident light, third light that is a part of the second light, in a second direction crossing the plane.

Further, in accordance with the present disclosure, there is provided an imaging apparatus including: a first branching optical system that separates first light belonging to a predetermined wavelength band from incident light in a first direction that is a surface direction of a plane including an optical axis corresponding to a normal direction of an incidence surface on which the incident light is incident; a second branching optical system that is provided subsequent to the first branching optical system and separates, from second light after the first light is separated from the incident light, third light that is a part of the second light, in a second direction crossing the plane; a first imaging element which is provided subsequent to the first branching optical system and on which the first light is focused; a second imaging element which is provided subsequent to the second branching optical system and on which at least a part of the third light is focused; and a third imaging element which is provided subsequent to the second branching optical system and on which at least a part of fourth light after the third light is separated from the second light is focused.

Further, in accordance with the present disclosure, there is provided an imaging system including: an optical system unit; and an imaging apparatus that captures an image acquired by the optical system unit. The imaging apparatus includes: a first branching optical system that separates first light belonging to a predetermined wavelength band from incident light in a first direction that is a surface direction of a plane including an optical axis corresponding to a normal direction of an incidence surface on which the incident light is incident; a second branching optical system that is provided subsequent to the first branching optical system and separates, from second light after the first light is separated from the incident light, third light that is a part of the second light, in a second direction crossing the plane; a first imaging element which is provided subsequent to the first branching optical system and on which the first light is focused; a second imaging element which is provided subsequent to the second branching optical system and on which at least a part of the third light is focused; and a third imaging element which is provided subsequent to the second branching optical system and on which at least a part of fourth light after the third light is separated from the second light is focused.

Advantageous Effects of Invention

As described above, in accordance with the present disclosure, there are provided a branching optical system, an imaging apparatus, and an imaging system in which a plurality of imaging elements can be efficiently disposed in a limited space in a configuration in which an image of a target is captured using the plurality of imaging elements.

Note that, the above-described effects are not necessarily limited, and any of the effects shown in this specification or other effects that can be grasped from this specification may be achieved together with the above-described effects or in place of the above-described effects.

BRIEF DESCRIPTION OF DRAWINGS

FIG. 11 is an explanatory diagram for describing an example of the configuration of an imaging apparatus according to Example 2.

MODE(S) FOR CARRYING OUT THE INVENTION

Figure 1:
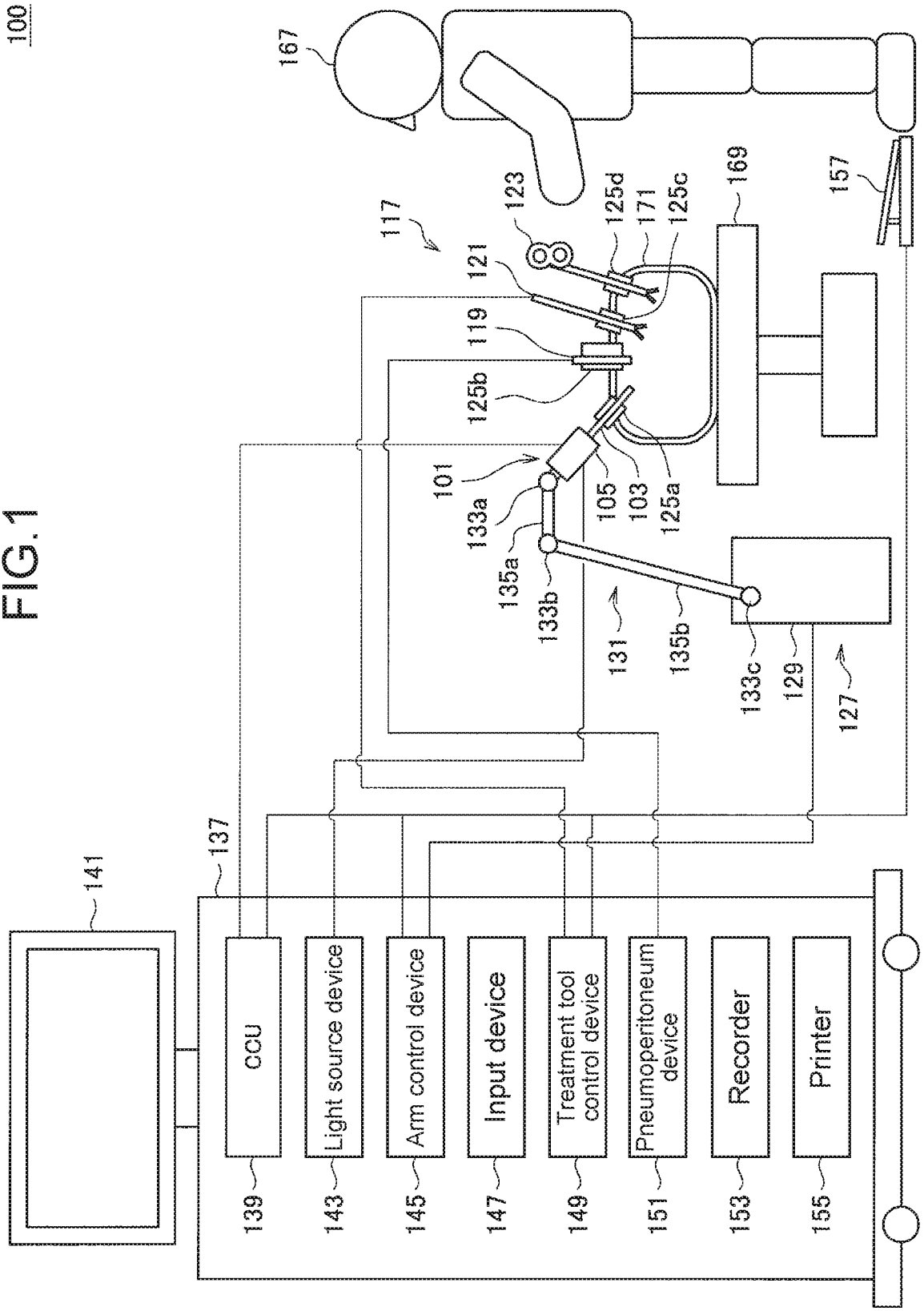
FIG. 1 is a diagram showing an example of the schematic configuration of an endoscopic imaging system according to an embodiment of the present disclosure.

Hereinafter, desirable embodiments of the present disclosure will be described in detail with reference to the accompanying diagrams. Note that, in this specification and the diagrams, components having substantially the same functional configurations are denoted by the same reference numerals, and the repeated description thereof will be omitted.

Note that, the description will be given in the following order.

1. Configuration example of an imaging system
2. Study on an imaging apparatus using a branching optical system
3. Technical features
  3.1. Configuration examples of an imaging apparatus
  3.2. Examples of an imaging apparatus
  3.3. Modification examples of an imaging apparatus
4. Examples of hardware configuration
5. Application examples
6. Conclusion <<1. Configuration Example of an Imaging System>>

First, as an example of the schematic configuration of an imaging system according to an embodiment of the present disclosure, an example of a case where the imaging system is configured as an endoscopic imaging system will be described with reference to FIGS. 1 and 2.

For example, FIG. 1 is a diagram showing an example of the schematic configuration of an endoscopic imaging system to which the technology according to the present disclosure can be applied, and shows an example of a case where the endoscopic imaging system is configured as a so-called endoscopic surgery system. FIG. 1 shows a state in which an operator (doctor) 167 performs a surgery on a patient 171 on a patient bed 169 using an endoscopic surgery system 100. As shown in the diagram, the endoscopic surgery system 100 includes an endoscope 101, other surgical tools 117, a support arm device 127 that supports the endoscope 101, and a cart 137 on which various devices for endoscopic surgery are mounted.

In endoscopic surgery, instead of cutting and opening the abdominal wall, a plurality of cylindrical opening tools called trocars 125a to 125d makes punctures in the abdominal wall. Then, a lens barrel 103 of the endoscope 101 and the other surgical tools 117 are inserted into the body cavity of the patient 171 through the trocars 125a to 125d. In the illustrated example, a pneumoperitoneum tube 119, an energy treatment tool 121, and forceps 123 are inserted into the body cavity of the patient 171 as the other surgical tools 117. Further, the energy treatment tool 121 is a treatment tool for performing dissection and peeling of tissue, sealing of a blood vessel, and the like by high-frequency current or ultrasonic vibration. However, the illustrated surgical tools 117 are merely examples, and various surgical tools generally used in endoscopic surgery, such as forceps and a retractor, may be used as the surgical tools 117, for example.

An image of a surgical part inside the body cavity of the patient 171 captured by the endoscope 101 is displayed on a display device 141. The operator 167 performs a treatment, such as excision of an affected part, using the energy treatment tool 121 and the forceps 123 while viewing the image of the surgical part displayed on the display device 141 in real time. Note that, although not shown, the pneumoperitoneum tube 119, the energy treatment tool 121, and the forceps 123 are supported by the operator 167 or an assistant during the surgery.

(Support Arm Device)

The support arm device 127 includes an arm unit 131 extending from a base unit 129. In the illustrated example, the arm unit 131 includes joint portions 133a, 133b, and 133c and links 135a and 135b, and is driven by the control of an arm control device 145. The endoscope 101 is supported by the arm unit 131, and its position and posture are controlled by the arm unit 131. Therefore, stable position fixation of the endoscope 101 can be realized.

(Endoscope)

The endoscope 101 includes the lens barrel 103 having a region of a predetermined length from the distal end that is inserted into the body cavity of the patient 171 and a camera head 105 connected to the proximal end of the lens barrel 103. In the illustrated example, the endoscope 101 configured as a so-called rigid endoscope having the rigid lens barrel 103 is illustrated. However, the endoscope 101 may be configured as a so-called flexible endoscope having the flexible lens barrel 103.

An opening into which an objective lens is fitted is provided at the distal end of the lens barrel 103. A light source device 143 is connected to the endoscope 101, and light generated by the light source device 143 is guided to the distal end of the lens barrel by a light guide extending in the lens barrel 103 and is emitted to an observation target (in other words, an imaging target) inside the body cavity of the patient 171 through the objective lens. Note that, the endoscope 101 may be a direct-view endoscope, a perspective endoscope, or a side-view endoscope.

An optical system and an imaging element are provided inside the camera head 105, and reflected light (observation light) from the observation target is condensed on the imaging element by the optical system. The observation light is photoelectrically converted by the imaging element to generate an electric signal corresponding to the observation light, that is, an image signal corresponding to the observation image. The image signal is transmitted to a camera control unit (CCU) 139 as RAW data. Note that, the camera head 105 has a function of adjusting the magnification and the focal length by driving the optical system appropriately.

Note that, in order to cope with stereoscopic viewing (3D display) and the like, a plurality of imaging elements may be provided in the camera head. In this case, a plurality of relay optical systems is provided inside the lens barrel 103 in order to guide observation light to each of the plurality of imaging elements.

(Various Devices Mounted on a Cart)

The CCU 139 is configured to include a central processing unit (CPU), a graphics processing unit (GPU), and the like, and performs overall control of the operations of the endoscope 101 and the display device 141. Specifically, the CCU 139 performs, for an image signal received from the camera head 105, various kinds of image processing for displaying an image based on the image signal, for example, development processing (demosaicing). The CCU 139 provides the display device 141 with the image signal subjected to the image processing. Further, the CCU 139 transmits a control signal to the camera head 105 to control the driving. The control signal may include information regarding the imaging conditions, such as a magnification and a focal length.

Under the control of the CCU 139, the display device 141 displays an image based on the image signal subjected to the image processing by the CCU 139. In a case where the endoscope 101 corresponds to high-resolution imaging, for example, 4K (horizontal pixel number 3840×vertical pixel number 2160) or 8K (horizontal pixel number 7680×vertical pixel number 4320), and/or a case where the endoscope 101 corresponds to 3D display, a display device capable of performing high-resolution display and/or a display device capable of performing 3D display can be used as the display device 141. In a case where the endoscope 101 corresponds to high-resolution imaging, such as 4K or 8K, a more immersive feeling can be obtained by using the display device 141 with a size of 55 inches or more. Further, a plurality of display devices 141 having different resolutions and sizes may be provided in a manner that depends on the application.

The light source device 143 is, for example, a light source such as a light emitting diode (LED), and supplies irradiation light for imaging a surgical part to the endoscope 101.

The arm control device 145 is, for example, a processor such as a CPU, and operates in accordance with a predetermined program to control the driving of the arm unit 131 of the support arm device 127 in accordance with a predetermined control method.

An input device 147 is an input interface with respect to the endoscopic surgery system 100. The user can input various kinds of information or instructions to the endoscopic surgery system 100 through the input device 147. For example, the user inputs various kinds of information regarding the surgery, such as physical information of the patient and information regarding the surgical method, through the input device 147. Further, for example, the user inputs an instruction to drive the arm unit 131, an instruction to change the imaging conditions (the type of irradiation light, the magnification and the focal length, and the like) of the endoscope 101, an instruction to drive the energy treatment tool 121, and the like through the input device 147.

The type of the input device 147 is not limited, and the input device 147 may be any known input device. As the input device 147, for example, a mouse, a keyboard, a touch panel, a switch, a foot switch 157, and/or a lever, can be applied. In a case where a touch panel is used as the input device 147, the touch panel may be provided on the display surface of the display device 141.

Alternatively, the input device 147 is, for example, a device installed by the user, such as a glasses type wearable device or a head mounted display (HMD), and various inputs are made in accordance with the user's gesture or eyes detected by these devices. Further, the input device 147 includes a camera capable of detecting the movement of the user, and various inputs are made in accordance with the user's gesture or eyes detected from an image captured by the camera. Furthermore, the input device 147 includes a microphone capable of picking up the user's voice, and various inputs are made by the voice through the microphone. As described above, since the input device 147 is configured to be capable of inputting various kinds of information in a non-contact manner, particularly a user (for example, the operator 167) belonging to a clean region can operate devices belonging to an unclean region in a non-contact manner. Further, since the user can operate the devices without removing his or her hands from the surgical tool he or she has, the convenience of the user is improved.

A treatment tool control device 149 controls the driving of the energy treatment tool 121 for performing cauterization and dissection of tissue, sealing of a blood vessel, and the like. A pneumoperitoneum device 151 sends gas into the body cavity through the pneumoperitoneum tube 119 to inflate the body cavity of the patient 171 for the purpose of securing a viewing field by the endoscope 101 and securing the working space of the operator. A recorder 153 is a device capable of recording various kinds of information regarding a surgery. A printer 155 is a device capable of printing various kinds of information regarding a surgery in various formats, such as a text, an image, and a graph.

Hereinafter, particularly characteristic configurations in the endoscopic surgery system 100 will be described in more detail.

(Support Arm Device)

The support arm device 127 includes the base unit 129, which is a pedestal, and the arm unit 131 extending from the base unit 129. In the illustrated example, the arm unit 131 includes a plurality of joint portions 133a, 133b, and 133c and a plurality of links 135a and 135b connected to each other by the joint portion 133b. In FIG. 1, however, the configuration of the arm unit 131 is simplified for the sake of convenience. In practice, the shapes, the number, and the arrangement of the joint portions 133a to 133c and the links 135a and 135b and the directions of rotation axes of the joint portions 133a to 133c can be appropriately set so that the arm unit 131 has a desired degree of freedom. For example, the arm unit 131 can be configured to have a degree of freedom of, desirably, 6 or more. Since this makes it possible to move the endoscope 101 freely within the movable range of the arm unit 131, it is possible to insert the lens barrel 103 of the endoscope 101 into the body cavity of the patient 171 from a desired direction.

Actuators are provided in the joint portions 133a to 133c, and the joint portions 133a to 133c are configured to be able to rotate around a predetermined rotation axis by driving the actuators. By controlling the driving of the actuators with the arm control device 145, the rotation angles of the joint portions 133a to 133c are controlled, so that the driving of the arm unit 131 is controlled. As a result, control of the position and posture of the endoscope 101 can be realized. In this case, the arm control device 145 can control the driving of the arm unit 131 by various known control methods, such as force control or position control.

For example, in accordance with an operation input that is appropriately performed by the operator 167 through the input device 147 (including the foot switch 157), the driving of the arm unit 131 may be appropriately controlled by the arm control device 145, so that the position and posture of the endoscope 101 are controlled. After moving the endoscope 101 at the distal end of the arm unit 131 from an arbitrary position to another arbitrary position by the control, the endoscope 101 can be fixedly supported at the position after the movement. Note that, the arm unit 131 may be operated by a so-called master slave method. In this case, the arm unit 131 can be remotely controlled by the user through the input device 147 installed at a location distant from the operating room.

Further, in a case where force control is applied, the arm control device 145 may perform so-called power assist control in which an external force from the user is received and the actuators of the joint portions 133a to 133c are driven so that the arm unit 131 moves smoothly following the external force. In this manner, when the user moves the arm unit 131 while directly touching the arm unit 131, the arm unit 131 can be moved with a relatively small force. Therefore, since it is possible to move the endoscope 101 more intuitively and with a simpler operation, the convenience of the user can be improved.

Here, in general, in endoscopic surgery, the endoscope 101 is supported by a doctor called a scopist. On the other hand, by using the support arm device 127, the position of the endoscope 101 can be more reliably fixed without manual operation. Therefore, since an image of the surgical part can be stably obtained, it is possible to perform the surgery smoothly.

Note that, the arm control device 145 may not necessarily be provided in the cart 137. Further, the arm control device 145 may not necessarily be one device. For example, the arm control device 145 may be provided in each of the joint portions 133a to 133c of the arm unit 131 of the support arm device 127, and the plurality of arm control devices 145 may cooperate with each other to realize the driving control of the arm unit 131.

(Light Source Device)

The light source device 143 supplies irradiation light for imaging the surgical part to the endoscope 101. The light source device 143 is, for example, a white light source configured by an LED, a laser light source, or a combination thereof. At this time, in a case where the white light source is configured by a combination of RGB laser light sources, the output intensity and the output timing of each color (each wavelength) can be controlled with high accuracy. Therefore, it is possible to adjust the white balance of the captured image in the light source device 143. Further, in this case, it is also possible to capture an image corresponding to each of RGB in a time division manner by emitting laser light from each of the RGB laser light sources to the observation target in a time division manner and controlling the driving of the imaging element of the camera head 105 in synchronization with the emission timing. In accordance with the method, it is possible to obtain a color image without providing a color filter in the imaging element.

Further, the driving of the light source device 143 may be controlled so that the intensity of light to be output is changed at predetermined time intervals. By acquiring images in a time division manner by controlling the driving of the imaging element of the camera head 105 in synchronization with the timing of a change in the light intensity and combining the images, it is possible to generate a high dynamic range image without blackout and overexposure.

Further, the light source device 143 may be configured to be able to supply light of a predetermined wavelength band corresponding to special light observation. In special light observation, for example, so-called narrow band imaging is performed to image a predetermined tissue, such as a blood vessel on the superficial layer of the mucous membrane, with high contrast by emitting narrow band light compared with irradiation light (that is, white light) at the time of normal observation using the wavelength dependency of light absorption in body tissue. Alternatively, in special light observation, fluorescence imaging may be performed to obtain an image by fluorescence generated by emitting excitation light. In the fluorescence imaging, excitation light can be emitted to body tissue and fluorescence from the body tissue can be observed (auto fluorescence imaging), or a reagent such as indocyanine green (ICG) can be locally injected into body tissue while emitting excitation light corresponding to the fluorescence wavelength of the reagent to the body tissue to obtain a fluorescence image. The light source device 143 can be configured to be able to supply narrow band light and/or excitation light corresponding to such special light observation.

(Camera Head and CCU)

The functions of the camera head 105 of the endoscope 101 and the CCU 139 will be described in more detail with reference to FIG. 2. FIG. 2 is a block diagram showing an example of the functional configurations of the camera head 105 and the CCU 139 shown in FIG. 1.

Figure 2:
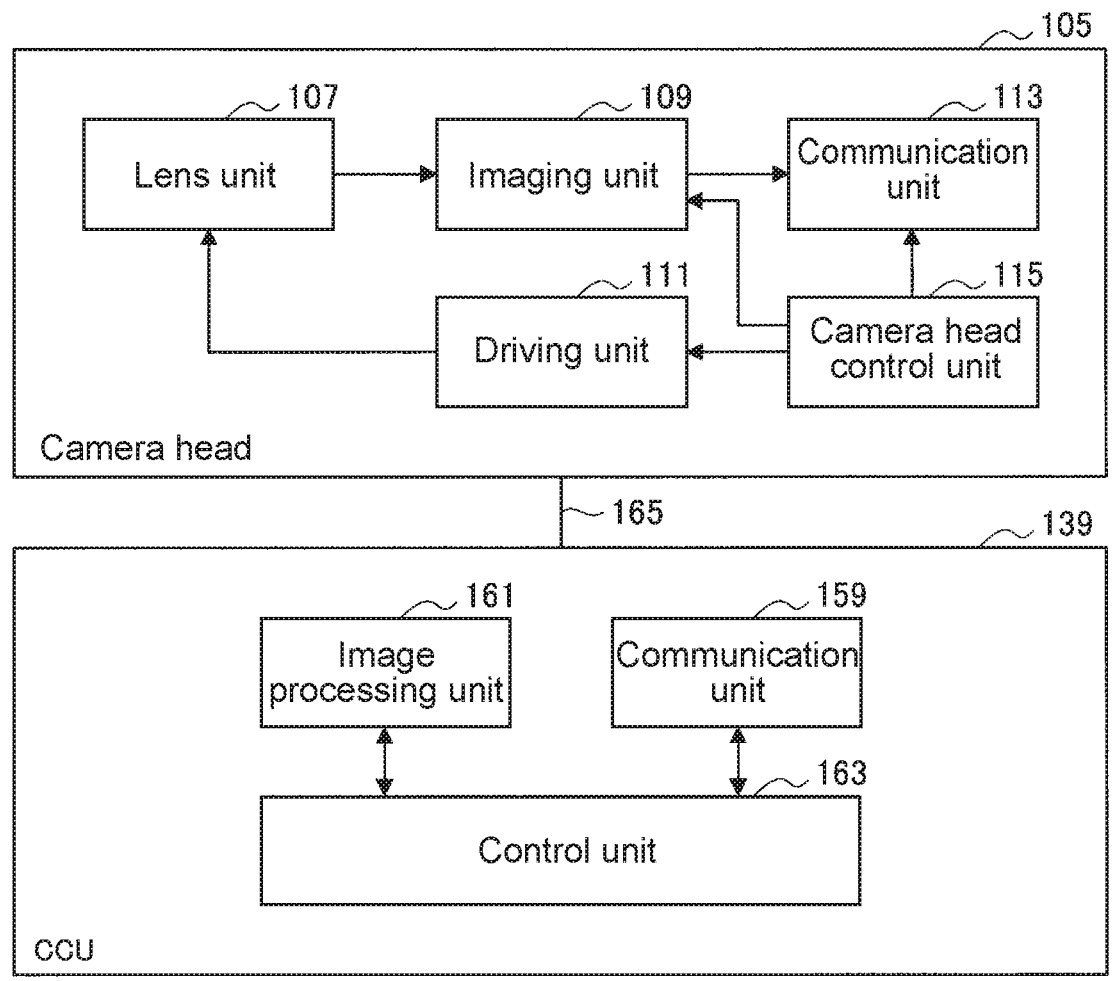
FIG. 2 is a block diagram showing an example of the functional configurations of a camera head and a CCU shown in FIG. 1.

Referring to FIG. 2, the camera head 105 has a lens unit 107, an imaging unit 109, a driving unit 111, a communication unit 113, and a camera head control unit 115 as its functions. Further, the CCU 139 has a communication unit 159, an image processing unit 161, and a control unit 163 as its functions. The camera head 105 and the CCU 139 are connected to each other so as to be able to communicate with each other bidirectionally by a transmission cable 165.

First, the functional configuration of the camera head 105 will be described. The lens unit 107 is an optical system provided at a portion of connection with the lens barrel 103. Observation light received from the distal end of the lens barrel 103 is guided to the camera head 105 and is incident on the lens unit 107. The lens unit 107 is configured by combining a plurality of lenses including a zoom lens and a focus lens. The optical characteristic of the lens unit 107 is adjusted so as to condense the observation light on the light receiving surface of the imaging element of the imaging unit 109. Further, the zoom lens and the focus lens are configured such that the position on the optical axis can be moved in order to adjust the magnification and the focus of the captured image.

The imaging unit 109 is configured by an imaging element, and is disposed subsequent to the lens unit 107. The observation light passing through the lens unit 107 is condensed on the light receiving surface of the imaging element, and an image signal corresponding to the observation image is generated by photoelectric conversion. The image signal generated by the imaging unit 109 is provided to the communication unit 113.

As an imaging element forming the imaging unit 109, for example, a complementary metal oxide semiconductor (CMOS) type image sensor, which has a Bayer arrangement and can perform color imaging, can be used. Note that, as the imaging element, an imaging element capable of capturing an image with a high resolution of, for example, 4K or more may be used. Since a high resolution image of the surgical part can be obtained, the operator 167 can check the situation of the surgical part in more detail. Therefore, it is possible to proceed with the surgery more smoothly.

Further, an imaging element forming the imaging unit 109 is configured to have a pair of imaging elements for acquiring image signals for the right eye and the left eye corresponding to 3D display. The 3D display enables the operator 167 to more accurately check the depth of the living tissue at the surgical part. Note that, in a case where the imaging unit 109 is configured as a multi-plate type, a plurality of lens units 107 is provided so as to correspond to respective imaging elements.

Further, the imaging unit 109 may not necessarily be provided in the camera head 105. For example, the imaging unit 109 may be provided immediately after the objective lens in the lens barrel 103.

The driving unit 111 is configured by an actuator, and moves the zoom lens and the focus lens of the lens unit 107 by a predetermined distance along the optical axis under the control of the camera head control unit 115. As a result, the magnification and the focus of the captured image by the imaging unit 109 can be appropriately adjusted.

The communication unit 113 is configured as a communication device for transmitting and receiving various kinds of information to and from the CCU 139. The communication unit 113 transmits an image signal obtained from the imaging unit 109 to the CCU 139 through the transmission cable 165 as RAW data. In this case, it is desirable that the image signal is transmitted by optical communication in order to display the captured image of the surgical part with low latency. This is because the operator 167 performs a surgery while observing the condition of the affected part in a captured image during the surgery and accordingly moving images of the surgical part are required to be displayed as real time as possible for safer and more reliable surgery. In a case where optical communication is performed, a photoelectric conversion module for converting an electric signal into an optical signal is provided in the communication unit 113. The image signal is converted into an optical signal by the photoelectric conversion module and is then transmitted to the CCU 139 through the transmission cable 165.

Further, the communication unit 113 receives a control signal for controlling the driving of the camera head 105 from the CCU 139. The control signal includes information regarding the imaging conditions, for example, information for designating the frame rate of the captured image, information for designating the exposure value at the time of imaging, and/or information for designating the magnification and the focus of the captured image. The communication unit 113 provides the received control signal to the camera head control unit 115. Note that, the control signal from the CCU 139 may also be transmitted by optical communication. In this case, a photoelectric conversion module for converting an optical signal into an electric signal is provided in the communication unit 113, and the control signal is converted into an electric signal by the photoelectric conversion module and is then provided to the camera head control unit 115.

Note that, the imaging conditions, such as the frame rate, the exposure value, the magnification, and the focus, are automatically set by the control unit 163 of the CCU 139 on the basis of the acquired image signal. That is, the endoscope 101 has so-called auto exposure (AE) function, auto focus (AF) function, and auto white balance (AWB) function.

The camera head control unit 115 controls the driving of the camera head 105 on the basis of the control signal from the CCU 139 received through the communication unit 113. For example, the camera head control unit 115 controls the driving of the imaging element of the imaging unit 109 on the basis of the information for designating the frame rate of the captured image and/or the information for designating the exposure at the time of imaging. Further, for example, the camera head control unit 115 appropriately moves the zoom lens and the focus lens of the lens unit 107 through the driving unit 111 on the basis of the information for designating the magnification and the focus of the captured image. The camera head control unit 115 may further have a function of storing information for identifying the lens barrel 103 or the camera head 105.

Note that, by arranging a structure, such as the lens unit 107 or the imaging unit 109, in a sealed structure with high airtightness and waterproofness, the camera head 105 can be made resistant to autoclave sterilization.

Next, the functional configuration of the CCU 139 will be described. The communication unit 159 is configured as a communication device for transmitting and receiving various kinds of information to and from the camera head 105. The communication unit 159 receives an image signal, which is transmitted through the transmission cable 165, from the camera head 105. At this time, as described above, the image signal can be appropriately transmitted by optical communication. In this case, a photoelectric conversion module for converting an optical signal into an electric signal is provided in the communication unit 159. The communication unit 159 provides the image signal converted into the electric signal to the image processing unit 161.

Further, the communication unit 159 transmits a control signal for controlling the driving of the camera head 105 to the camera head 105. The control signal may also be transmitted by optical communication.

The image processing unit 161 performs various kinds of image processing on the image signal that is RAW data transmitted from the camera head 105. Examples of the image processing include various kinds of known signal processing, such as development processing, high image quality processing (band emphasis processing, super resolution processing, noise reduction (NR) processing, and/or camera shake correction processing), and/or enlargement processing (electronic zoom processing). Further, the image processing unit 161 performs detection processing on the image signal to perform AE, AF, and AWB.

The image processing unit 161 is a processor, such as a CPU or a GPU, and the image processing or the detection processing described above can be performed by the processor that operates in accordance with a predetermined program. Note that, in a case where the image processing unit 161 is configured by a plurality of GPUs, the image processing unit 161 appropriately divides information regarding the image signal and performs image processing in parallel by the plurality of GPUs.

The control unit 163 performs various kinds of control regarding the imaging of the surgical part by the endoscope 101 and the display of the captured image. For example, the control unit 163 generates a control signal for controlling the driving of the camera head 105. At this time, in a case where the imaging conditions are input by the user, the control unit 163 generates a control signal on the basis of the input by the user. Alternatively, in a case where the endoscope 101 has the AE function, the AF function, and the AWB function, the control unit 163 generates a control signal by appropriately calculating an optimal exposure value, an optimal focal length, and an optimal white balance in accordance with the result of the detection processing by the image processing unit 161.

Further, the control unit 163 displays an image of the surgical part on the display device 141 on the basis of the image signal subjected to the image processing by the image processing unit 161. In this case, the control unit 163 recognizes various objects in the surgical part image using various image recognition technologies. For example, the control unit 163 can recognize surgical tools such as forceps, a specific living part, bleeding, mist when using the energy treatment tool 121, and the like by detecting the shape, color, and the like of an edge of an object included in the surgical part image. When displaying the image of the surgical part on the display device 141, the control unit 163 displays various kinds of surgery support information so as to be superimposed on the image of the surgical part using the recognition result. Since the surgery support information is superimposed and presented to the operator 167, it is possible to proceed with the surgery more safely and reliably.

The transmission cable 165 connecting the camera head 105 and the CCU 139 to each other is an electric signal cable corresponding to electric signal communication, an optical fiber corresponding to optical communication, or a composite cable thereof.

Here, in the illustrated example, wired communication is performed using the transmission cable 165. However, communication between the camera head 105 and the CCU 139 may be performed wirelessly. In a case where the communication between the camera head 105 and the CCU 139 is performed wirelessly, it is not necessary to provide the transmission cable 165 in the operating room. Therefore, a situation in which the movement of the medical staff in the operating room is obstructed by the transmission cable 165 can be eliminated.

Up to now, an example of the endoscopic surgery system 100 to which the technology according to the present disclosure can be applied has been described. Note that, although the endoscopic surgery system 100 has been described as an example herein, the system to which the technology according to the present disclosure can be applied is not limited to this example. For example, the technology according to the present disclosure may be applied to a flexible endoscope system for an examination or a microsurgery system.

<<2. Study on an Imaging Apparatus Using a Branching Optical System>>

Subsequently, as an example of an imaging apparatus applied to an imaging system, such as the endoscopic surgery system 100 described with reference to FIGS. 1 and 2, an example of the configuration of an imaging apparatus using a branching optical system will be described. Then, problems of the imaging apparatus according to the present embodiment will be described.

In a field where a medical imaging system, such as the endoscopic surgery system 100 described with reference to FIGS. 1 and 2, is applied, there is a need for a mechanism capable of capturing an image with higher color reproducibility or resolution as an image of a target that is a subject. As an example of an imaging apparatus capable of capturing an image with higher color reproducibility or resolution as described above, an imaging apparatus in which the light use efficiency is further improved by using a color separation optical system (for example, a color separation prism) can be mentioned. Specifically, in the imaging apparatus, light from the target is separated into a plurality of spectral components by the color separation optical system and the separated spectral components are focused on different imaging elements, so that a captured image of the target is generated on the basis of the images captured by the respective imaging elements. With such a configuration, for example, since it is not necessary to apply a color filter and the like, it is possible to further improve the light use efficiency. Therefore, it is possible to obtain an image with high color reproducibility or resolution.

Figure 3:
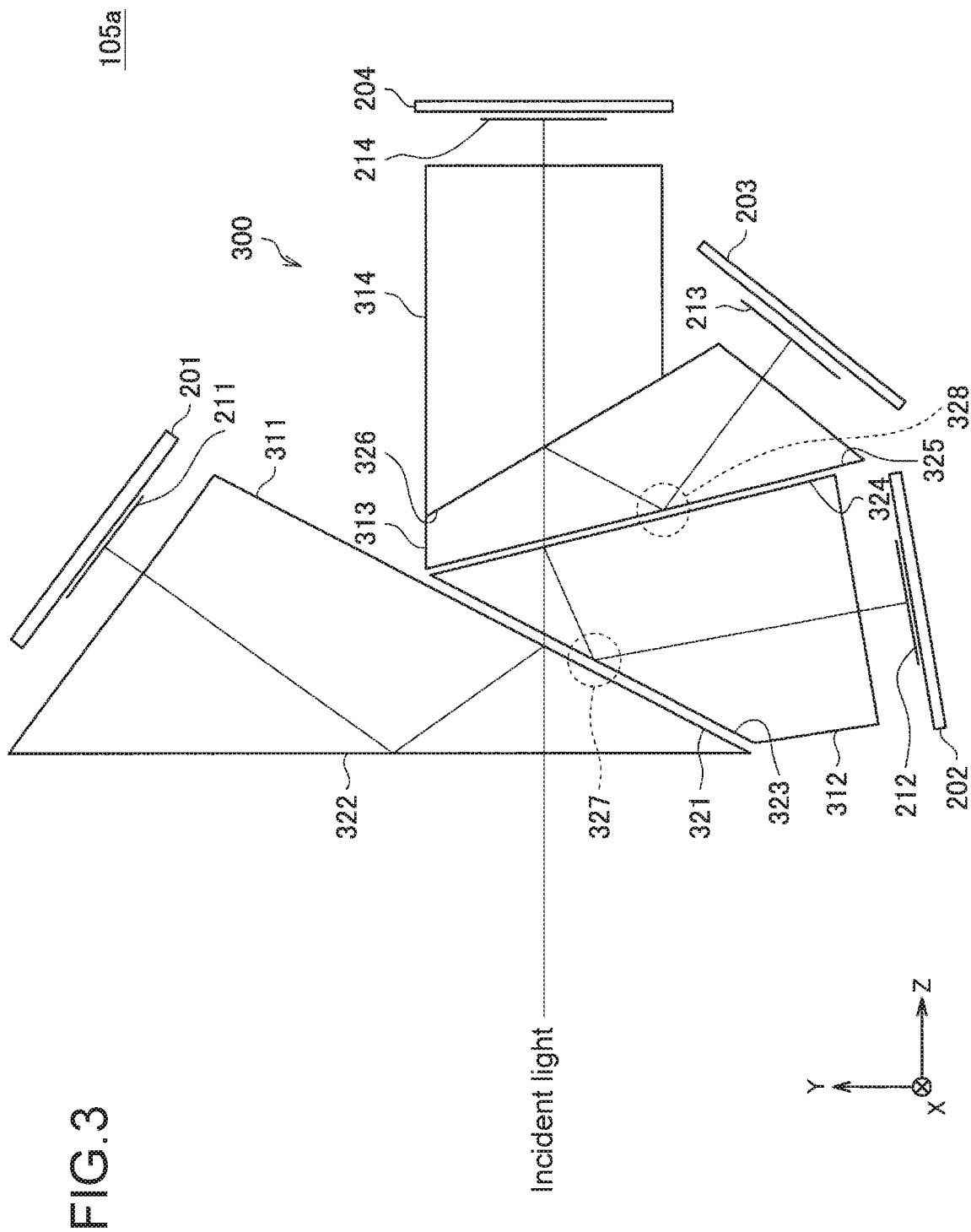
FIG. 3 is an explanatory diagram for describing an example of the configuration of an imaging apparatus according to a comparative example.

As the imaging apparatus using a color separation optical system as described above, for example, an imaging apparatus using a three-color separation optical system that separates light from a target into an R component, a G component, and a B component can be mentioned. Further, in recent years, an imaging apparatus using a four-color separation optical systems has also been proposed. Therefore, as a comparative example, an example of the schematic configuration of an imaging apparatus using a four-color separation optical system will be described with reference to FIG. 3 focusing particularly on the configuration until light incident on the imaging apparatus is focused on the imaging element. FIG. 3 is an explanatory diagram for describing an example of the configuration of an imaging apparatus according to a comparative example, and shows an example of an imaging apparatus that can be applied as the camera head 105 of the endoscopic surgery system 100 described above. Note that, in the following description, the imaging apparatus shown in FIG. 3 may be referred to as an "imaging apparatus 105a" in order to explicitly distinguish the imaging apparatus from other imaging apparatuses applicable as the camera head 105.

Note that, in FIG. 3, the z direction corresponds to the optical axis direction of light (that is, incident light) incident on the imaging apparatus 105a, and the x direction and the y direction are directions perpendicular to the z direction. Further, the x direction and the y direction are assumed to be perpendicular to each other. That is, in FIG. 3, the horizontal direction of the diagram corresponds to the z direction. Further, in FIG. 3, the depth direction of the diagram corresponds to the x direction, and the vertical direction of the diagram corresponds to the y direction. Note that, in FIG. 3, the x direction corresponds to the horizontal direction of the imaging apparatus 105a, and the y direction corresponds to the vertical direction of the imaging apparatus 105a.

As shown in FIG. 3, the imaging apparatus 105a includes a branching optical system 300, first to fourth imaging elements 211 to 214, and substrates 201 to 204. The first to fourth imaging elements 211 to 214 are held by the substrates 201 to 204, respectively.

The branching optical system 300 is an optical member that separates light (that is, incident light) incident on the imaging apparatus 105a into a plurality of spectral components having different wavelength bands. For example, in the example shown in FIG. 3, the branching optical system 300 separates the incident light into light components of three primary colors of an R component, a G component, and a B component and light of a near infrared (IR) component. Specifically, as shown in FIG. 3, the branching optical system 300 is configured by sequentially assembling first to fourth prisms 311 to 314 in the optical axis direction (z direction) of incident light.

The first prism 311 is a prism that functions as an optical path for guiding light belonging to the near infrared wavelength band, among the light components incident on the first prism 311, to the first imaging element 211. The incident light incident on the imaging apparatus 105a enters the first prism 311 from an incidence surface 322 of the first prism 311. Further, the incident light that has entered the first prism 311 travels straight through the first prism 311 and is separated into light belonging to the visible light wavelength band and light belonging to the near infrared wavelength band on a surface 321 provided obliquely on the optical axis. Note that, an optical film (for example, a dichroic film) for separating incident light into light belonging to the visible light wavelength band and light belonging to the near infrared wavelength band may be provided on the surface 321.

The light belonging to the near infrared wavelength band is reflected on the surface 321 and guided through the first prism 311. Here, the reflected and separated light belonging to the near infrared wavelength band (that is, near infrared light) is totally reflected only once on the incidence surface 322 and transmitted to the outside of the first prism 311. For example, in the example shown in FIG. 3, the light belonging to the near infrared wavelength band is reflected on the surface 321 in the surface direction of the yz plane. Then, the near infrared light transmitted through the first prism 311 is guided to the first imaging element 211. Note that, the first imaging element 211 is disposed such that the light receiving surface is perpendicular to the optical axis of the light (that is, near infrared light) transmitted through the first prism 311 and guided to the first imaging element 211. Further, as the first imaging element 211, for example, an imaging element in which no color filter is provided and which has high sensitivity for the near infrared wavelength may be more desirably applied.

Further, the light belonging to the visible light wavelength band transmitted through the surface 321 of the first prism 311 is incident on the second prism 312 from the incidence surface 323 of the second prism 312. The second prism 312 is a prism that functions as an optical path for guiding light belonging to the wavelength band including the B component, among the light components incident on the second prism 312, to the second imaging element 212. The light (that is, light belonging to the visible light wavelength band) incident on the second prism 312 travels straight through the second prism 312 and is separated into light belonging to the short wavelength side wavelength band including the B component and light belonging to the long wavelength side wavelength band including the R component and the G component on a surface 324 provided obliquely on the optical axis. Note that, an optical film (for example, a dichroic film) for separating incident light into light belonging to the short wavelength side wavelength band including the B component and light belonging to the long wavelength side wavelength band including the R component and the G component may be provided on the surface 324.

The light belonging to the wavelength band including the B component is reflected on the surface 324 and guided through the second prism 312. Here, as shown in FIG. 3, an air gap is provided between the surface 321 of the first prism 311 and the incidence surface 323 of the second prism 312 as indicated by reference numeral 327. For this reason, the light belonging to the wavelength band including the B component reflected and separated on the surface 324 is totally reflected only once on the incidence surface 323 and transmitted to the outside of the second prism 312. For example, in the example shown in FIG. 3, the light belonging to the wavelength band including the B component is reflected on the surface 324 in the surface direction of the yz plane. Then, the light belonging to the wavelength band including the B component transmitted through the second prism 312 is guided to the second imaging element 212. Note that, the second imaging element 212 is disposed such that the light receiving surface is perpendicular to the optical axis of the light (that is, light belonging to the wavelength band including the B component) transmitted through the second prism 312 and guided to the second imaging element 212.

Further, the light belonging to the wavelength band including the R component and the G component transmitted through the surface 323 of the second prism 312 is incident on the third prism 313 from the incidence surface 325 of the third prism 313. The third prism 313 is a prism that functions as an optical path for guiding light belonging to the wavelength band including the R component, among the light components incident on the third prism 313, to the third imaging element 213. The light (that is, light belonging to the wavelength band including the R component and the G component) incident on the third prism 313 travels straight through the third prism 313 and is separated into light belonging to the wavelength band including the R component and light belonging to the wavelength band including the G component at an interface 326 with the fourth prism 314 provided obliquely on the optical axis. Note that, an optical film (for example, a dichroic film) for separating incident light into light belonging to the wavelength band including the R component and light belonging to the wavelength band including the G component may be provided on the interface 326.

The light belonging to the wavelength band including the R component is reflected at the interface 326 and guided through the third prism 313. Here, as shown in FIG. 3, an air gap is provided between the surface 324 of the second prism 312 and the incidence surface 325 of the third prism 313 as indicated by reference numeral 328. For this reason, the light belonging to the wavelength band including the R component reflected and separated at the interface 326 is totally reflected only once on the incidence surface 325 and transmitted to the outside of the third prism 313. For example, in the example shown in FIG. 3, the light belonging to the wavelength band including the R component is reflected at the interface 326 in the surface direction of the yz plane.

Then, the light belonging to the wavelength band including the R component transmitted through the third prism 313 is guided to the third imaging element 213. Note that, the third imaging element 213 is disposed such that the light receiving surface is perpendicular to the optical axis of the light (that is, light belonging to the wavelength band including the R component) transmitted through the third prism 313 and guided to the third imaging element 213.

Further, the light belonging to the wavelength band including the G component transmitted through the interface 326 between the third prism 313 and the fourth prism 314 is incident on the fourth prism 314 from the interface 326. The fourth prism 314 is a prism that functions as an optical path for guiding light (that is, light belonging to the wavelength band including the R component) incident on the fourth prism 314 to the fourth imaging element 214. That is, the light incident on the fourth prism 314 travels straight through the fourth prism 314 and is guided to the fourth imaging element 214. Note that, the fourth imaging element 214 is disposed such that the light receiving surface is perpendicular to the optical axis of the light (that is, light belonging to the wavelength band including the G component) transmitted through the fourth prism 314 and guided to the fourth imaging element 214.

As described above, the imaging apparatus 105a according to the comparative example separates the incident light into light components of three primary colors of the R component, the G component, and the B component and light of the IR component and focuses the respective light components on different imaging elements (that is, the first to fourth imaging elements 211 to 214), thereby separately capturing images based on the respective light components. With such a configuration, in the imaging apparatus 105a, since it is not necessary to provide a color filter in each imaging element, it is possible to improve the light use efficiency. Therefore, compared with an imaging apparatus in which a color separation optical system is not used (that is, an imaging apparatus that captures an image with one imaging element), it is possible to capture an image with further improved color reproducibility or resolution.

Further, in the imaging apparatus 105a according to the comparative example, since the light components of three primary colors of the R component, the G component, and the B component and the light of the IR component are focused on different imaging elements, it is possible to separately capture a near infrared image and a visible light image at the same timing. Such a configuration is expected to be applied to an observation method called so-called special light observation, such as narrow band imaging (NBI), auto fluorescence imaging (AFI), and infra-red imaging (IRI), in the medical field.

As a specific example, in the fluorescence imaging, a fluorescent substance having affinity for a lesion such as cancer is administered to a person to be examined (patient) in advance, and excitation light for exciting the fluorescent substance is emitted, so that a lesion portion is observed by a fluorescence image of fluorescence emitted from the fluorescent substance accumulated in the lesion portion (that is, an observation image based on the detection result of the fluorescence). Indocyanine green (ICG) can be mentioned as a typical example of the fluorescent substance used for the fluorescence imaging. The ICG emits fluorescence (that is, light in the near infrared band) having a wavelength of around 820 nm by using light having a wavelength near 808 nm as excitation light.

Therefore, for example, by applying an imaging apparatus using a four-color separation optical system to the fluorescence imaging, it is possible to capture a fluorescence image of a target by an imaging element on which light of the IR component is focused and to capture a visible light image of the target with high resolution by another imaging element. Further, since it is possible to separately capture a fluorescence image and a visible light image of the target at the same timing, for example, a fluorescence image captured in synchronization with a visible light image can be superimposed on the visible light image.

On the other hand, in the imaging apparatus using a color separation optical system, it is necessary to dispose the color separation optical system and each imaging element so that physical interference does not occur between a plurality of imaging elements on which light components separated by the color separation optical system are focused. For this reason, in the imaging apparatus using a color separation optical system, as the number of imaging elements increases (that is, as the number of spectral components to be separated (for example, the number of colors) increases), the size of the color separation optical system increases. As a result, the flange back length tends to increase.

Note that, in this description, the "flange back length" indicates an optical distance from the mount surface of a lens to an imaging element in a lens replacement type imaging apparatus. As a specific example, in the case of the example shown in FIG. 3, the optical distance from the incidence surface of the branching optical system 300 to each imaging element corresponds to the flange back length. Further, the "optical distance" corresponds to an optical distance calculated from the traveling speed of light, and is calculated by the physical distance of the light path and the refractive index in the path.

Due to such characteristics, for example, in the imaging apparatus using a four-color separation optical system, such as the imaging apparatus 105a according to the comparative example, the size of the color separation optical system and the flange back length may be larger than those in the imaging apparatus using a three color separation optical system. For this reason, in the lens replacement type imaging apparatus using a four color separation optical system, usable lenses may be limited to those having a relatively long flange back length.

On the other hand, as lenses applied to an endoscope, a surgical microscope, and the like in the medical field, those having a standard called "C mount" have become the mainstream. In the standard, the flange back length is defined as 17.526 mm. Further, in the medical field, there is a demand for miniaturization of various medical devices so as not to obstruct medical practice, and imaging apparatuses are no exception. As an imaging apparatus satisfying such conditions, for example, one using a three-color separation optical system is provided. However, due to constraints of the size or the flange back length described above, it is difficult to apply the imaging apparatus using a four-color separation optical system to an endoscope or a surgical microscope instead of an existing imaging apparatus (for example, an imaging apparatus using a three-color separation optical system).

In view of such a situation, in the present disclosure, an example of a mechanism for suppressing an increase in the size of a housing or the flange back length by efficiently disposing a plurality of imaging elements in a limited space, in a configuration in which an image of a target is captured by the plurality of imaging elements by using a color separation optical system, will be proposed.

<<3. Technical Features>>

Hereinafter, technical features of the imaging apparatus according to the present embodiment will be described.

<3.1. Configuration Examples of an Imaging Apparatus>

Figure 4:
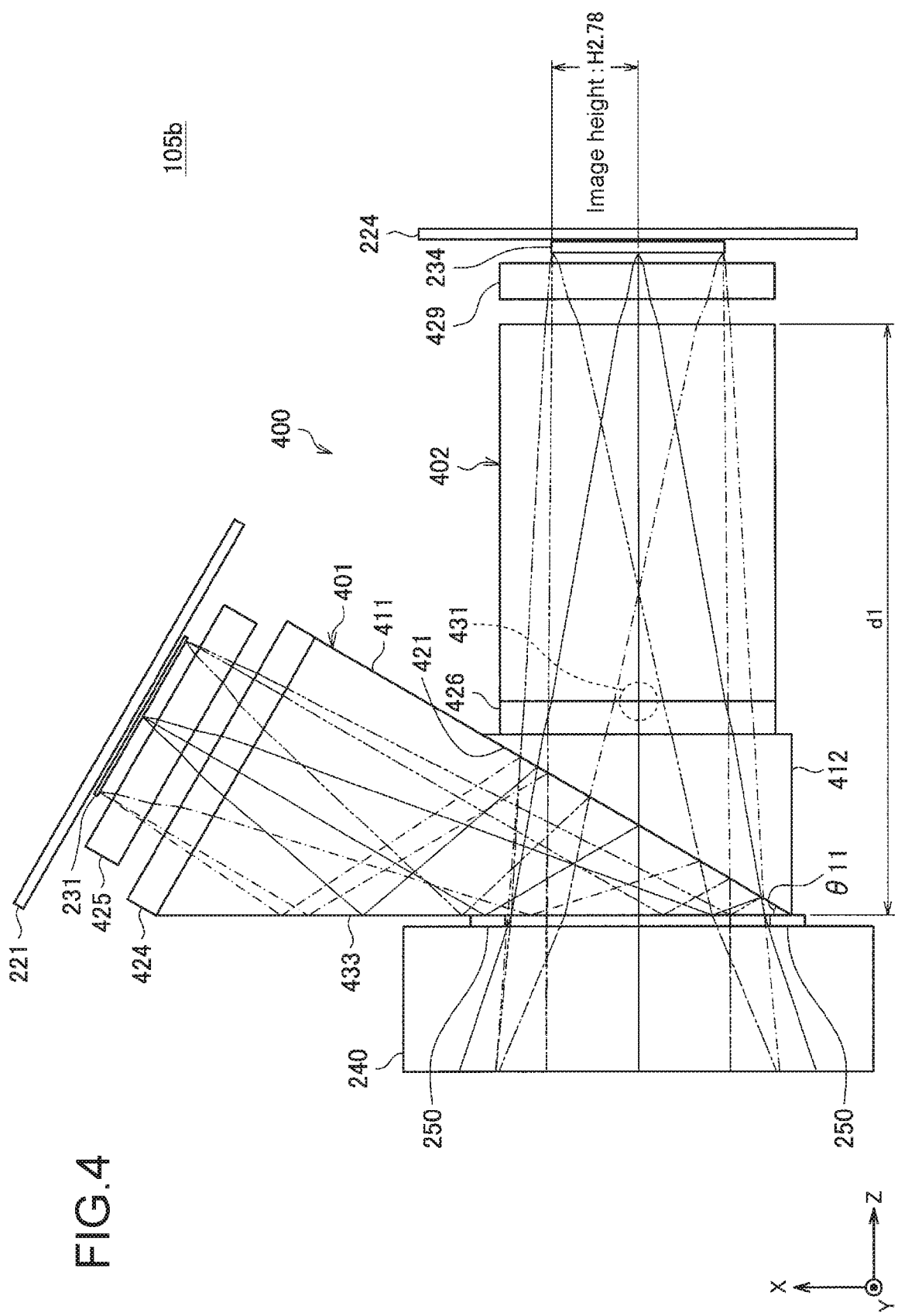
FIG. 4 is an explanatory diagram for describing an example of the configuration of an imaging apparatus according to an embodiment of the present disclosure.
Figure 5:
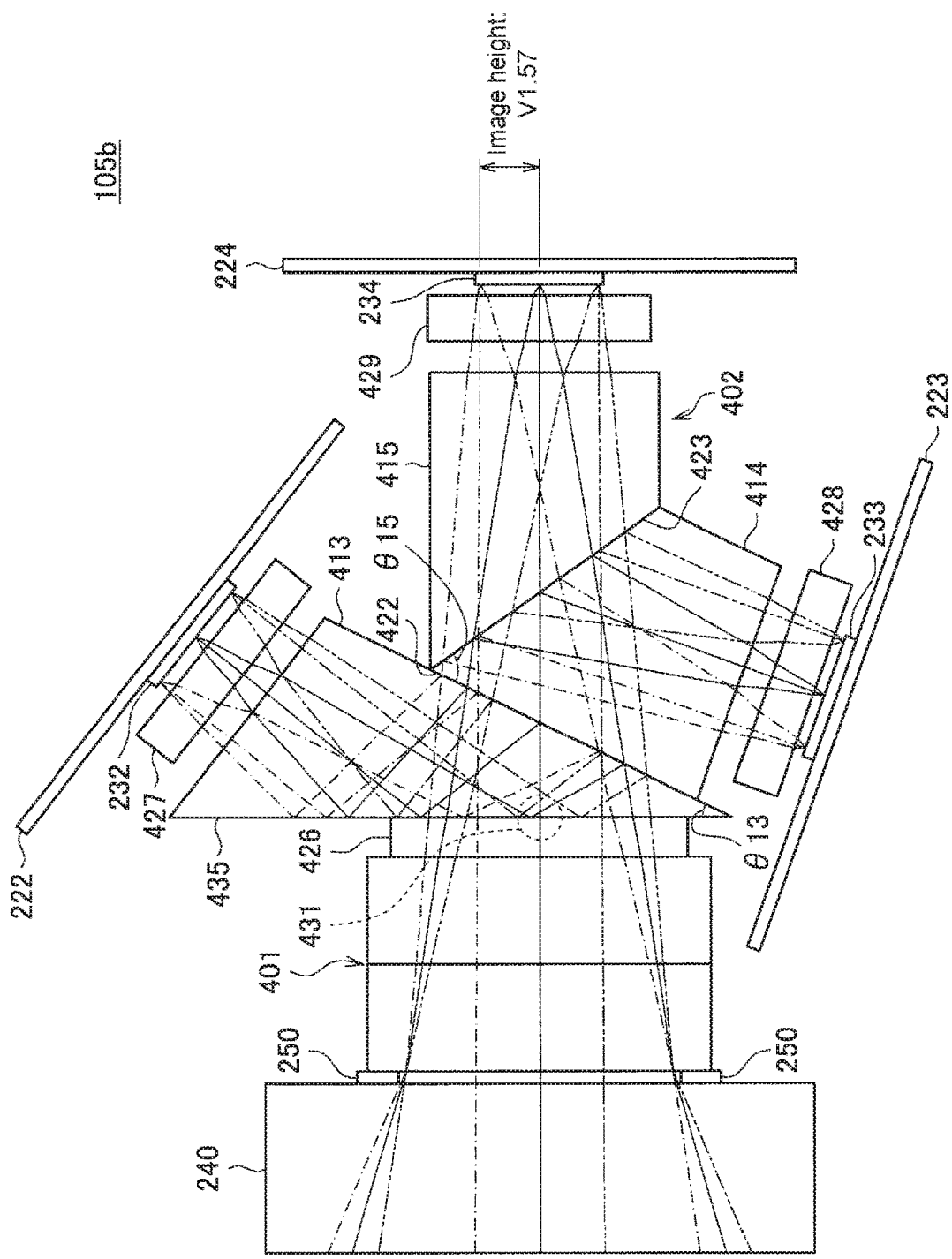
FIG. 5 is an explanatory diagram for describing an example of the configuration of an imaging apparatus according to an embodiment of the present disclosure.

First, an example of the schematic configuration of the imaging apparatus according to the present embodiment will be described with reference to FIGS. 4 and 5 focusing particularly on the configuration until light incident on the imaging apparatus is focused on the imaging element. FIGS. 4 and 5 are explanatory diagrams for describing an example of the configuration of the imaging apparatus according to the present embodiment, and show an example of an imaging apparatus that can be applied as the camera head 105 of the endoscopic surgery system 100 described above. Note that, in this description, it is assumed that the imaging apparatus according to the present embodiment is configured as an imaging apparatus based on the C mount standard. Further, in the following description, the imaging apparatus shown in FIGS. 4 and 5 may be referred to as an "imaging apparatus 105b" in order to explicitly distinguish the imaging apparatus from other imaging apparatuses applicable as the camera head 105.

As shown in FIGS. 4 and 5, the imaging apparatus 105b according to the present embodiment includes a mount base 240, a branching optical system 400, first to fourth imaging elements 231 to 234, and substrates 221 to 224. The first to fourth imaging elements 231 to 234 are held by the substrates 221 to 224, respectively. Further, the imaging apparatus 105b may include an opening mask 250, or may include cover glasses 425 and 427 to 429.

Note that, in FIGS. 4 and 5, the z direction corresponds to the optical axis direction of light (that is, incident light) incident on the imaging apparatus 105b, in other words, the normal direction of the incidence surface of the branching optical system 400 that will be described in detail later. Further, it is assumed that both the x direction and the y direction are directions perpendicular to the z direction and the x direction and the y direction are perpendicular to each other. Note that, in FIGS. 4 and 5, the x direction corresponds to the horizontal direction of the imaging apparatus 105b, and the y direction corresponds to the vertical direction of the imaging apparatus 105b. Further, FIG. 4 schematically shows the configuration of the imaging apparatus 105b in a case where the imaging apparatus 105b is cut along a horizontal plane (xz plane) including the optical axis (z axis) of incident light, and also shows the optical path of light incident on the imaging apparatus 105b. That is, in FIG. 4, the horizontal direction, the vertical direction, and the depth direction of the diagram correspond to the z direction, the x direction, and the y direction, respectively. Further, FIG. 5 schematically shows the configuration of the imaging apparatus 105b in a case where the imaging apparatus 105b is cut along a vertical plane (yz plane) including the optical axis (z axis) of incident light, and also shows the optical path of light incident on the imaging apparatus 105b. That is, in FIG. 5, the horizontal direction, the vertical direction, and the depth direction of the diagram correspond to the z direction, the y direction, and the x direction, respectively.

The mount base 240 is configured to attach an optical system, such as a replacement type lens, a microscope, or an endoscope, to the imaging apparatus 105b. An opening through which light from a target incident from an optical system attached to the mount base 240 passes is formed in the mount base 240. That is, light from the target condensed by the optical system attached to the mount base 240 enters the imaging apparatus 105b from the opening of the mount base 240.

An opening having a predetermined shape is provided in the opening mask 250. By the opening, the light flux of light (that is, incident light) incident on the imaging apparatus 105b through the optical system attached to the mount base 240 is limited. The opening provided in the opening mask 250 is formed in, for example, a rectangular shape having a dimension corresponding to the size of the light receiving surface of each imaging element (that is, each of the first to fourth imaging elements 231 to 234). That is, the F number is determined in accordance with the dimension of the opening provided in the opening mask 250. Further, in the opening mask 250, for example, a mechanism called a so-called "stop" that controls the dimension of an opening by changing the diameter of the opening with the optical axis of incident light as the center may be provided. For example, as shown in FIGS. 4 and 5, the opening mask 250 is provided so as to be interposed between the mount base 240 and the branching optical system 400.

Note that, since an imaging lens (for example, a replacement type lens, a microscope, or an endoscope) attached to the imaging apparatus 105b is optically designed to be image-side telecentric, the F number of the entire imaging system is determined by the dimension of the opening mask 250 and the configuration of the optical system (for example, a glass material, a thickness, and an air gap) disposed after the opening mask 250.

Subsequently, the branching optical system 400 will be described. As shown in FIGS. 4 and 5, the branching optical system 400 includes a first branching optical system 401, a second branching optical system 402, and an IR cut filter 426. Further, the branching optical system 400 may include a band pass filter 424.

The first branching optical system 401 separates light incident on the first branching optical system 401 into light belonging to the near infrared wavelength band and light belonging to the visible light wavelength band. Specifically, as shown in FIG. 4, the first branching optical system 401 is a prism in which a first prism 411 and a second prism 412 are connected to each other with a dichroic film 421 interposed therebetween. That is, the dichroic film 421 is provided at the interface between the first prism 411 and the second prism 412.

The dichroic film 421 is an optical film that separates incident light, which is incident on the first branching optical system 401 and includes light belonging to the visible light wavelength band and light belonging to the near infrared wavelength band, into light belonging to the visible light wavelength band and light belonging to the near infrared wavelength band. Specifically, the dichroic film 421 has a characteristic of reflecting light belonging to the near infrared wavelength band and transmitting light belonging to the visible light wavelength band.

Figure 6:
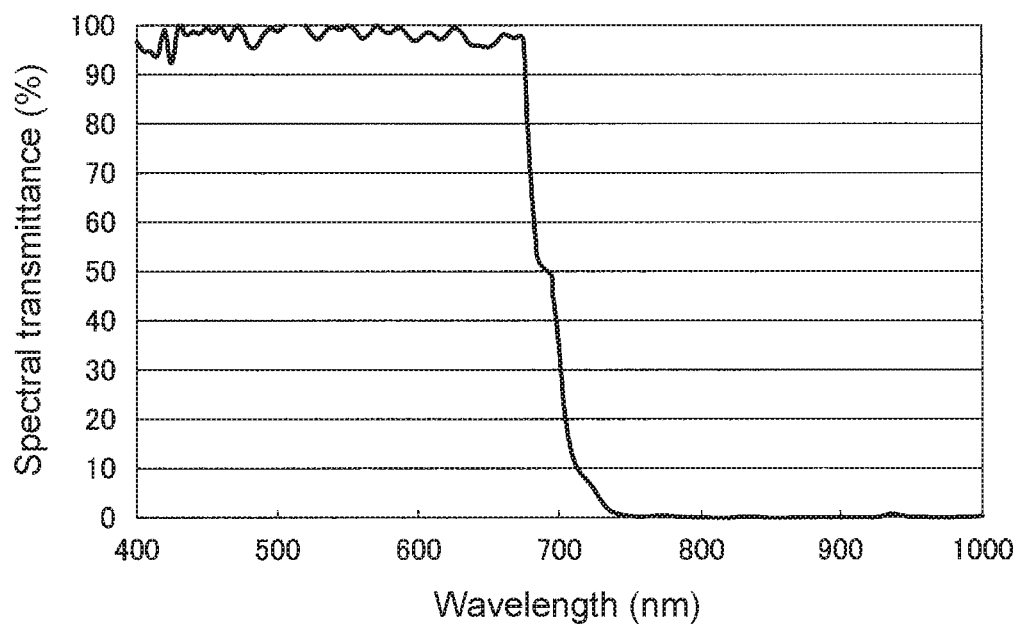
FIG. 6 is a diagram showing an example of the spectral characteristics of a dichroic film applied to the imaging apparatus according to the same embodiment.

For example, FIG. 6 is a diagram showing an example of the spectral characteristics of the dichroic film 421 applied to the imaging apparatus according to the present embodiment. In FIG. 6, the horizontal axis indicates a wavelength (nm), and the vertical axis indicates a spectral transmittance (%). As shown in FIG. 6, the dichroic film 421 has a characteristic of transmitting most (for example, 90% or more) of the light on the short wavelength side and reflecting most (for example, 90% or more) of the light on the long wavelength side with a wavelength near 700 nm as a boundary.

The first prism 411 is a prism on which light belonging to the visible light wavelength band and light (that is, incident light) belonging to the near infrared wavelength band are incident and which functions as an optical path for near infrared light through which the light belonging to the near infrared wavelength band is guided. Further, the second prism 412 is a prism that functions as an optical path for visible light through which the light belonging to the visible light wavelength band is guided.

The incident light that has entered the first prism 411 from an incidence surface 433 travels straight through the first prism 411 and is separated into light belonging to the visible light wavelength band and light belonging to the near infrared wavelength band by the dichroic film 421 provided obliquely on the optical axis.

The light belonging to the near infrared wavelength band is reflected by the dichroic film 421 and guided through the first prism 411. More specifically, in the example shown in FIG. 4, the light belonging to the near infrared wavelength band is reflected in the surface direction of a plane (that is, the xz plane) including the optical axis (that is, the z axis) corresponding to the normal direction of the incidence surface 433, on which incident light to the branching optical system 400 is incident, by the dichroic film 421. Note that, the light reflected by the dichroic film 421 corresponds to an example of "first light", and the reflection direction corresponds to an example of "first direction".

Here, as shown in FIG. 4, the reflected and separated light belonging to the near infrared wavelength band (hereinafter, also referred to as "near infrared light") is totally reflected only once on the incidence surface 433 and transmitted to the outside of the first prism 411. In this manner, the angle of the film forming surface of the dichroic film 421 with respect to the optical axis can be made to be approximately 90°. Conversely, the installation angle of the dichroic film 421 according to the present embodiment on the optical axis is set such that the total reflection conditions described above are satisfied. By arranging the dichroic film 421 in this manner, even in a case where light of a large F value is incident on the first prism 411, it is possible to suppress a change in the spectral characteristics of the dichroic film 421 due to the difference in incidence angle between left light and right light. Therefore, it is possible to perform wavelength separation with high accuracy.

The near infrared light transmitted through the first prism 411 is guided to the first imaging element 231. In this case, the band pass filter 424 may be provided in the optical path of light separated by the dichroic film 421 and focused on the first imaging element 231. The band pass filter 424 has a characteristic of transmitting light in a predetermined wavelength band in the near infrared wavelength band and blocking light in the other wavelength bands. The band pass filter 424 may be disposed in accordance with the characteristics of the fluorescent substance in consideration of, for example, a situation in which the imaging apparatus 105b is used in the fluorescence imaging using a fluorescent substance that emits fluorescence in a predetermined wavelength band in the near infrared wavelength band.

Figure 7:
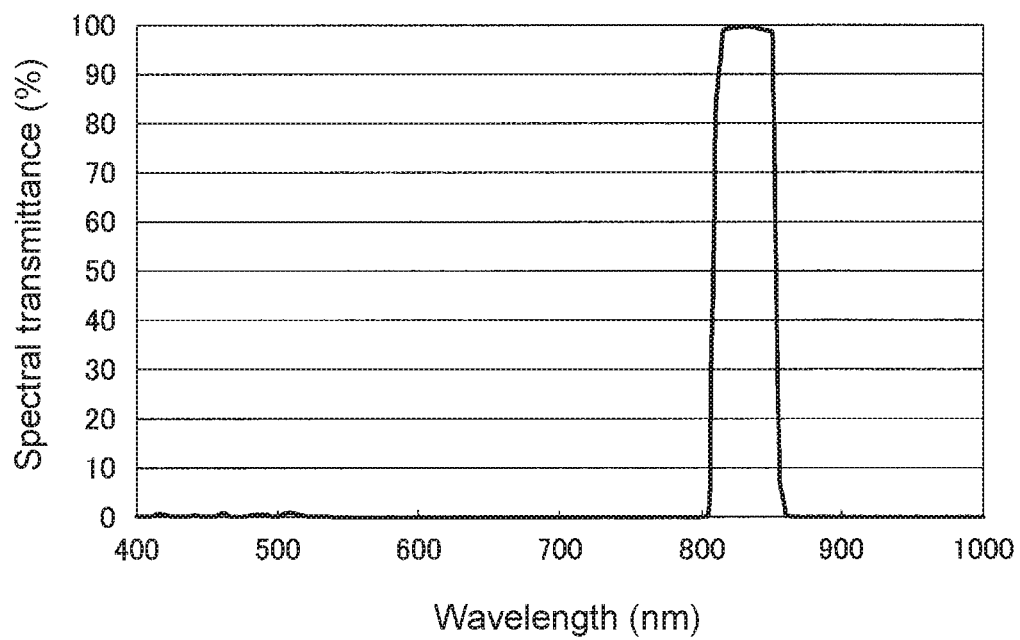
FIG. 7 is a diagram showing an example of the spectral characteristics of a band pass filter applied to the imaging apparatus according to the same embodiment.

As a specific example, in the case of focusing on the fluorescence emitted by the ICG, the band pass filter 424 may have a characteristic of transmitting light in a wavelength band (for example, a wavelength band of 820 nm to 850 nm) around 820 nm, which is a wavelength band of fluorescence emitted by the ICG, and blocking light in other wavelength bands. For example, FIG. 7 is a diagram showing an example of the spectral characteristics of the band pass filter 424 applied to the imaging apparatus according to the present embodiment. In FIG. 7, the horizontal axis indicates a wavelength (nm), and the vertical axis indicates a spectral transmittance (%). As shown in FIG. 7, the band pass filter 424 has a characteristic of transmitting most (for example, 90% or more) of the light in a wavelength band near 820 nm to 850 nm and reflecting most (for example, 90% or more) of the light in other wavelength bands.

The first imaging element 231 is disposed such that the light receiving surface is perpendicular to the optical axis of the light (that is, near infrared light) transmitted through the first prism 411 and guided to the first imaging element 231. Note that, a cover glass 425 for protecting the light receiving surface of the first imaging element 231 may be interposed between the first prism 411 and the first imaging element 231. As the cover glass 425, for example, one using a glass material generally known as BK7 is applied. Further, as the first imaging element 231, for example, an imaging element in which no color filter is provided and which has high sensitivity for the near infrared wavelength may be more desirably applied.

On the other hand, the light belonging to the visible light wavelength band transmitted through the dichroic film 421 is incident on the second prism 412 and travels straight through the second prism 412. The end surface of the second prism 312 opposite to a side on which the dichroic film 421 is provided (in other words, the emission surface of the second prism 412 on the downstream side of the optical axis) is provided perpendicular to the optical axis. The light belonging to the visible light wavelength band is transmitted to the outside of the second prism 412 while maintaining a state in which the light belonging to the visible light wavelength band is perpendicular to the emission surface of the second prism 412. Note that, the light transmitted through the dichroic film 421 corresponds to an example of "second light".

The second branching optical system 402 is connected to the emission surface of the second prism 412 with the IR cut filter 426 interposed therebetween. That is, the IR cut filter 426 is provided the interface between the second prism 412 of the first branching optical system 401 and the second branching optical system 402.

Figure 8:
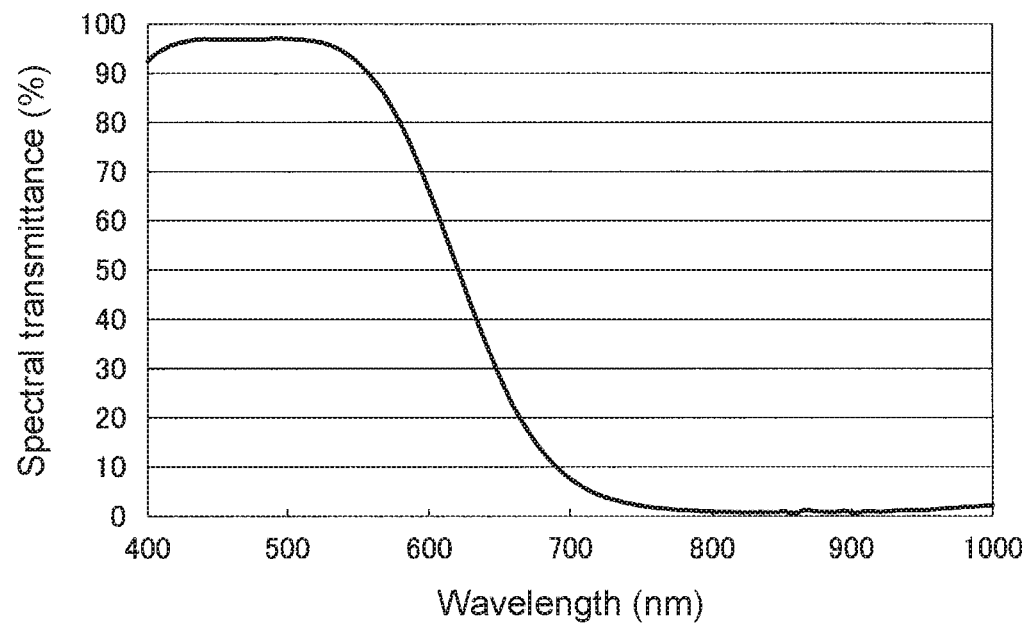
FIG. 8 is a diagram showing an example of the spectral characteristics of an IR cut filter applied to the imaging apparatus according to the same embodiment.

The IR cut filter 426 is a filter that cuts infrared light. For example, FIG. 8 is a diagram showing an example of the spectral characteristics of the IR cut filter 426 applied to the imaging apparatus according to the present embodiment. In FIG. 8, the horizontal axis indicates a wavelength (nm), and the vertical axis indicates a spectral transmittance (%). As shown in FIG. 8, the IR cut filter 426 has a characteristic of absorbing most (for example, 90% or more) of the light in a wavelength band longer than 700 nm and reflecting light in other wavelength bands. Note that, the IR cut filter 426 may be formed, for example, by depositing an infrared cut coat on a glass material equivalent to BK7. Further, as another example, the IR cut filter 426 may be formed of infrared absorbing glass. Note that, as the IR cut filter 426, for example, C5000 manufactured by Hoya Co., Ltd. can be used.

Note that, although not shown in detail in FIGS. 4 and 5, an air gap is provided at the interface between the IR cut filter 426 and the second branching optical system 402 as indicated by reference numeral 431.

Subsequently, mainly with reference to FIG. 5, the configuration of each unit located subsequent to the IR cut filter 426 will be described. Light belonging to the visible light wavelength band emitted from the second prism 412 of the first branching optical system 401 is incident on the second branching optical system 402 after infrared light is cut by the IR cut filter 426.

The second branching optical system 402 separates the light belonging to the visible light wavelength band incident on the second branching optical system 402 into light components belonging to a wavelength band including each of the R component, the G component, and the B component. Specifically, the second branching optical system 402 is a prism in which a third prism 413 and a fourth prism 414 are connected to each other with a dichroic film 422 interposed therebetween and the fourth prism 414 and a fifth prism 415 are connected to each other with a dichroic film 423 interposed therebetween. That is, the dichroic film 422 is provided at the interface between the third prism 413 and the fourth prism 414, and the dichroic film 423 is provided at the interface between the fourth prism 414 and the fifth prism 415.

The dichroic film 422 is an optical film that separates incident light, which is incident on the second branching optical system 402 and includes light belonging to the visible light wavelength band, into light belonging to a wavelength band including the G component and light belonging to a wavelength band including the R component and the B component. Specifically, the dichroic film 422 has a characteristic of reflecting the light belonging to the wavelength band including the G component and transmitting the light belonging to the short wavelength side wavelength band including the R component and the B component.

Further, the dichroic film 423 is an optical film that separates incident light, which is transmitted through the dichroic film 422 and includes light belonging to the wavelength band including the R component and the B component, into light belonging to a wavelength band including the R component and light belonging to a wavelength band including the B component. Specifically, the dichroic film 423 has a characteristic of reflecting the light belonging to the wavelength band including the B component and transmitting the light belonging to the wavelength band including the R component.

The third prism 413 is a prism on which light belonging to the visible light wavelength band is incident and which functions as an optical path for green light through which the light belonging to the wavelength band including the G component is guided. Further, the fourth prism 414 is a prism on which light belonging to the wavelength band including the R component and the B component is incident and which functions as an optical path for blue light through which the light belonging to the wavelength band including the B component is guided. Further, the fifth prism 415 is a prism that functions as an optical path for red light through which the light belonging to the wavelength band including the R component is guided.

The light belonging to the visible light wavelength band incident on the third prism 413 from an incidence surface 435 travels straight through the third prism 413 and is separated into light belonging to the wavelength band including the G component and light belonging to the wavelength band including the R component and the B component by the dichroic film 422 provided obliquely on the optical axis.

The light belonging to the wavelength band including the G component is reflected by the dichroic film 422 and guided through the third prism 413. At this time, the dichroic film 422 reflects the light belonging to the wavelength band including the G component in a direction twisted relative to a direction, in which the dichroic film 421 described above reflects the light belonging to the near infrared wavelength band, with the optical axis (that is, the z axis) of the incident light to the branching optical system 400 as its axis. That is, as shown in FIG. 4, in a case where the dichroic film 421 reflects the light belonging to the near infrared wavelength band in the surface direction of the xz plane, the dichroic film 422 reflects the light belonging to the wavelength band including the G component in a direction crossing the xz plane. As a specific example, in the example shown in FIG. 5, the dichroic film 422 reflects the light belonging to the long wavelength side wavelength band including the G component in the surface direction of a horizontal plane (that is, the yz plane where the xz plane and the normal direction are perpendicular to each other) including the z direction. In other words, in the example shown in FIG. 5, the dichroic film 422 reflects the light belonging to the long wavelength side wavelength band including the G component in a direction approximately perpendicular to each of the optical axis of the incident light to the branching optical system 400 and a direction in which the dichroic film 421 reflects the light belonging to the near infrared wavelength band. Note that, the light reflected by the dichroic film 422 corresponds to an example of "third light", and the reflection direction corresponds to an example of "second direction".

Here, the light belonging to the wavelength band including the reflected and separated G component (hereinafter, also referred to as "green light") reaches the incidence surface 435, as shown in FIG. 5. Further, as described above, an air gap is provided between the incidence surface 435 and the IR cut filter 426 as indicated by reference numeral 431. Therefore, the green light is totally reflected only once at the incidence surface 435 and transmitted to the outside of the third prism 413. In this manner, the angle of the film forming surface of the dichroic film 422 with respect to the optical axis can be made to be approximately 90°. Conversely, the installation angle of the dichroic film 422 according to the present embodiment on the optical axis is set such that the total reflection conditions described above are satisfied. By arranging the dichroic film 422 in this manner, even in a case where light of a large F value is incident on the third prism 413, it is possible to suppress a change in the spectral characteristics of the dichroic film 422 due to the difference in incidence angle between upper light and lower light. Therefore, it is possible to perform wavelength separation with high accuracy.

The green light transmitted through the third prism 413 is guided to the second imaging element 232. The second imaging element 232 is disposed such that the light receiving surface is perpendicular to the optical axis of the light transmitted through the third prism 413 and guided to the second imaging element 232. Note that, a cover glass 427 for protecting the light receiving surface of the second imaging element 232 may be interposed between the third prism 413 and the second imaging element 232. As the cover glass 425, the same one as the cover glass 425 described above can be applied. Further, as the second imaging element 232, for example, an imaging element in which no color filter is provided and which has high sensitivity for the wavelength band including the G component may be more desirably applied.

On the other hand, the light belonging to the wavelength band including the R component and the B component transmitted through the dichroic film 422 is incident on the fourth prism 414. Then, the light incident on the fourth prism 414 travels straight through the fourth prism 414 and is separated into light belonging to the wavelength band including the R component and light belonging to the wavelength band including the B component by the dichroic film 423 provided obliquely on the optical axis. Note that, the light transmitted through the dichroic film 422 corresponds to an example of "fourth light".

The light belonging to the wavelength band including the B component is reflected by the dichroic film 423 and guided through the fourth prism 414. At this time, the dichroic film 423 reflects the light belonging to the wavelength band including the B component in a direction twisted relative to a direction, in which the dichroic film 421 described above reflects the light belonging to the near infrared wavelength band, with the optical axis (that is, the z axis) of the incident light to the branching optical system 400 as its axis. That is, as shown in FIG. 4, in a case where the dichroic film 421 reflects the light belonging to the near infrared wavelength band in the surface direction of the xz plane, the dichroic film 422 reflects the light belonging to the wavelength band including the B component in a direction crossing the xz plane. As a specific example, in the example shown in FIG. 5, the dichroic film 423 reflects the light belonging to the wavelength band including the B component in the surface direction of a horizontal plane (that is, the yz plane where the xz plane and the normal direction are perpendicular to each other) including the z direction, the surface direction being a direction different from the direction in which the dichroic film 422 reflects the green light. Note that, the light reflected by the dichroic film 423 corresponds to an example of "fifth light", and the reflection direction corresponds to an example of "third direction". Further, in the example described above, the xz plane corresponds to an example of "first plane", and the yz plane corresponds to an example of "second plane".

The light belonging to the wavelength band including the reflected and separated B component (hereinafter, also referred to as "blue light") is guided through the fourth prism 414. Further, the blue light transmitted through the fourth prism 414 is guided to the third imaging element 233. The third imaging element 233 is disposed such that the light receiving surface is perpendicular to the optical axis of the light transmitted through the fourth prism 414 and guided to the third imaging element 233. Note that, a cover glass 428 for protecting the light receiving surface of the third imaging element 233 may be interposed between the fourth prism 414 and the third imaging element 233. As the cover glass 428, the same one as the cover glass 425 described above can be applied. Further, as the third imaging element 233, for example, an imaging element in which no color filter is provided and which has high sensitivity for the wavelength band including the B component may be more desirably applied.

Further, the light belonging to the wavelength band including the R component transmitted through the dichroic film 423 (hereinafter, also referred to as "red light") is incident on the fifth prism 415 and travels straight through the fifth prism 415. The end surface of the fifth prism 415 opposite to a side on which the dichroic film 423 is provided (in other words, the emission surface of the fifth prism 415 on the downstream side of the optical axis) is provided perpendicular to the optical axis. The red light is transmitted to the outside of the fifth prism 415 while maintaining a state in which the red light is perpendicular to the emission surface of the fifth prism 415. Then, the red light transmitted through the fifth prism 415 is guided to the fourth imaging element 234. The fourth imaging element 234 is disposed such that the light receiving surface is perpendicular to the optical axis of the light transmitted through the fifth prism 415 and guided to the fourth imaging element 234. Note that, a cover glass 429 for protecting the light receiving surface of the fourth imaging element 234 may be interposed between the fifth prism 415 and the fourth imaging element 234. As the cover glass 429, the same one as the cover glass 425 described above can be applied. Further, as the fourth imaging element 234, for example, an imaging element in which no color filter is provided and which has high sensitivity for the wavelength band including the R component may be more desirably applied.

Figure 9:
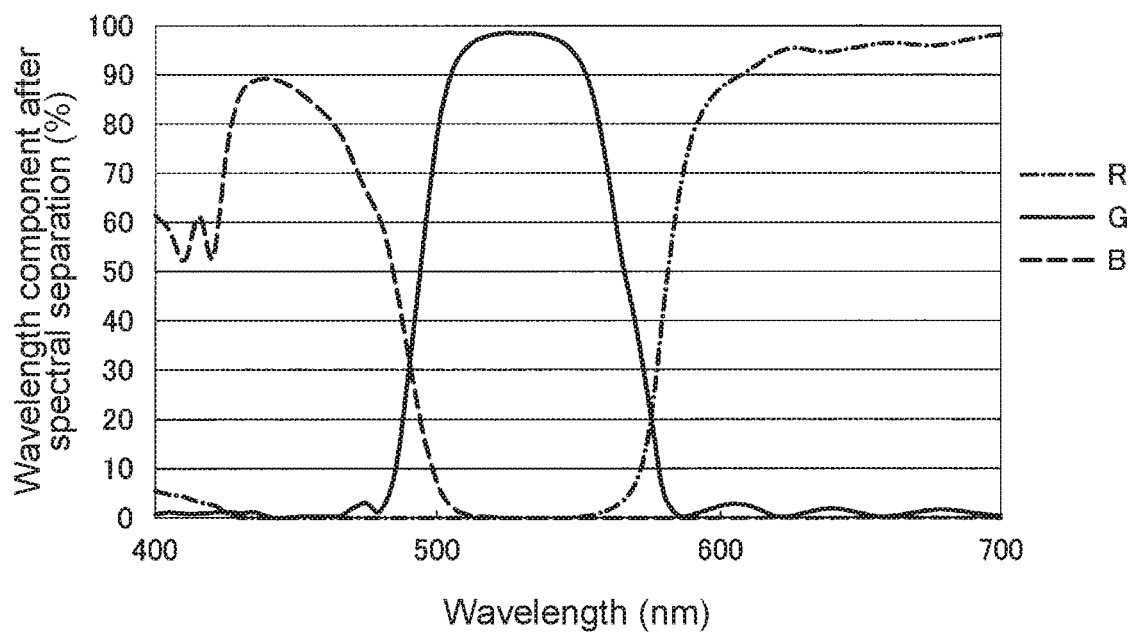
FIG. 9 is a diagram showing an example of the wavelength characteristic of each of light components that are separated from light belonging to a visible light wavelength band by a branching optical system according to the same embodiment.

With the above-described configuration, the visible light incident on the second branching optical system 402 is separated into red light, green light, and blue light by the second branching optical system 402, and the red light, the green light, and the blue light are focused on the fourth imaging element 234, the second imaging element 232, and the third imaging element 233, respectively. For example, FIG. 9 is a diagram showing an example of the wavelength characteristic of each of light components, which are separated from the light belonging to the visible light wavelength band, by the branching optical system 400 according to the present embodiment, and shows an example of the wavelength characteristic of red light (R), green light (G), and blue light (B). In FIG. 9, the horizontal axis indicates a wavelength (nm), and the vertical axis indicates a wavelength component included in each light component after spectral separation that is expressed as a relative value (%) with respect to incident light. That is, as the dichroic films 422 and 423, those having spectral characteristics to separate incident light into respective light components so that light components (that is, green light, blue light, and red light) focused on the second to fourth imaging elements 232 to 234 show the characteristics shown in FIG. 9 may be applied.

As described above with reference to FIGS. 4 and 5, the imaging apparatus 105*b* according to the present embodiment separates incident light into a plurality of light components and focuses the respective light components on different imaging elements using the branching optical system 400 including the first branching optical system 401 and the second branching optical system 402. At this time, the first branching optical system 401 and the second branching optical system 402 separate some of the incident light by reflecting some of the incident light in directions twisting each other with the optical axis corresponding to the normal direction of the incidence surface 433, on which light is incident on the branching optical system 400, as its axis.

With such a configuration, in the imaging apparatus 105*b* according to the present embodiment, it is possible to avoid physical interference between the substrate 221 that supports the first imaging element 231 and the substrates 222 to 224 that support the second to fourth imaging elements 232 to 234, respectively. That is, in the imaging apparatus 105*b* according to the present embodiment, it is possible to efficiently dispose the first to fourth imaging elements 231 to 234 (in other words, the substrates 221 to 224) in a limited space.

Further, in the imaging apparatus 105*b* according to the present embodiment, it is possible to reduce the number of places where an air gap is formed compared with the imaging apparatus 105*a* according to the comparative example shown in FIG. 3. The formation of an air gap may be a cause of defects due to dust and the like entering the air gap. For this reason, a design with fewer air gaps is desirable. That is, in the imaging apparatus 105*b* according to the present embodiment, it is possible to further reduce the possibility of the occurrence of a defect due to the formation of the air gap compared with the imaging apparatus 105*a* according to the comparative example.

Note that, the configuration described above is merely an example, and the configuration of the imaging apparatus 105*b* according to the present embodiment is not necessarily limited to the examples described above. As a specific example, as long as some of the incident light can be focused on the first to fourth imaging elements 231 to 234, the correspondence relationship between each imaging element and light focused on the imaging element is not limited. Further, it is needless to say that a configuration (for example, an optical film, such as the dichroic films 421 to 423) for separating some of the incident light may be appropriately selected in accordance with the correspondence relationship between each imaging element and light focused on the imaging element. Further, the configuration for separating some of the incident light is not limited to the optical film that separates the incident light in accordance with the wavelength characteristic, such as a dichroic film, and, for example, other optical films, such as a half mirror film, can also be applied. Note that, an example in which the half mirror film is applied will be separately described later as a modification example.

Further, in the above, as the imaging apparatus 105b according to the present embodiment, an example of the configuration of an imaging apparatus using a four-color separation optical system has been described focusing particularly on the configuration of the branching optical system 400. On the other hand, the examples described above are merely examples, and the configuration of the branching optical system 400 is not necessarily limited to the examples described above as long as the first branching optical system 401 and the second branching optical system 402 are configured to reflect some of the incident light in directions twisting each other with the optical axis of the incident light to the branching optical system 400 as its axis. For example, the imaging apparatus 105b according to the present embodiment can be configured as an imaging apparatus using a three-color separation optical system. In this case, as the second branching optical system 402, a branching optical system that branches the optical path of the incident light into two optical paths may be applied instead of the branching optical system that branches the optical path of the incident light into three optical paths as shown in FIGS. 4 and 5. Further, as another example, the first branching optical system 401 may be configured to branch the optical path of the incident light into three optical paths, similarly to the second branching optical system 402.

Up to now, an example of the schematic configuration of the imaging apparatus according to the present embodiment has been described with reference to FIGS. 4 and 5 focusing particularly on the configuration until light incident on the imaging apparatus is focused on the imaging element.

<3.2. Examples of an Imaging Apparatus>

Subsequently, examples of the imaging apparatus according to the present embodiment will be described.

EXAMPLE 1

First, as Example 1, an example of a more detailed configuration of the imaging apparatus 105b shown in FIGS. 4 and 5 will be described. Note that, in this example, an example of a case will be described in which the imaging apparatus 105b according to the present embodiment is configured as an imaging apparatus based on the C mount standard. That is, in Example 1, in order to satisfy the flange back length conditions (17.526 mm) defined by the C mount standard, an example of the configuration of the imaging apparatus 105b will be described in which the optical distance from at least the incidence surface of the branching optical system 400 to the imaging element located subsequent to the branching optical system 400 is 17.526 mm or less.

As shown in FIGS. 4 and 5, in the imaging apparatus 105b according to Example 1, the size (that is, image height) of an image formed on each of imaging elements (that is, the first to fourth imaging elements 231 to 234) is 3.14 mm in the vertical direction and 5.56 mm in the horizontal direction. For this reason, in FIG. 4, the optical path of light focused at each position of −2.78 mm and +2.78 mm, at the center, in the horizontal direction of the light receiving surface of each imaging element is shown. Similarly, in FIG. 5, the optical path of light focused at each position of −1.57 mm and +1.57 mm, at the center, in the vertical direction of the light receiving surface of each imaging element is shown. The F number at the center of the light receiving surface of each imaging element is Fno_H=1.57 in the horizontal direction and Fno_V=1.78 in the vertical direction. Further, the opening provided in the opening mask 250 is formed in a rectangular shape having a size of 8.2 mm in the horizontal direction (x direction) and a size of 7.2 mm in the vertical direction (y direction).

Further, in the imaging apparatus 105b according to Example 1, a glass material satisfying the conditions of refractive index Nd≥1.80 is applied as a glass material forming the first to fifth prisms 411 to 415 configuring the branching optical system 400. As a specific example, a case will be described in which a glass material satisfying the conditions of refractive index Nd=1.804200 and Abbe number vd=46.5025 is used as a glass material forming the first to fifth prisms 411 to 415. Note that, as a glass material satisfying the same conditions, for example, TAF3 manufactured by Hoya Co., Ltd. can be mentioned.

Further, as the cover glasses 425 and 427 to 429, for example, those having a thickness of 1.2 mm using BK7 as a glass material are used. Further, each of the band pass filter 424 and the IR cut filter 426 has a thickness of 1.09 mm in the optical axis direction. Further, the refractive index Nd of each of the band pass filter 424 and the IR cut filter 426 is equivalent to that of BK7.

In FIG. 4, the angle denoted by reference numeral θ11, that is, the angle between the incidence surface 433 of the first prism 411 and the surface, on which the dichroic film 421 is formed, on the xz plane is 30°. Further, in FIG. 5, the angle denoted by reference numeral θ13, that is, the angle between the incidence surface 435 of the third prism 413 and the surface, on which the dichroic film 422 is formed, on the yz plane is 25.75°. Further, in FIG. 5, the angle denoted by reference numeral θ15, that is, the angle between the surface on which the dichroic film 422 is formed and the surface on which the dichroic film 423 is formed on the yz plane is 60.75°.

Here, when the glass thickness of the branching optical system 400 is defined as the width (physical distance) of the branching optical system 400 in the z direction, the glass thickness d1 of the branching optical system 400 in the imaging apparatus 105b according to Example 1 is 18.844 mm. That is, the imaging apparatus 105b according to Example 1 can be formed so that the glass thickness d1 of the branching optical system 400 is larger than 17.526 mm while satisfying the flange back length conditions (17.526 mm) defined by the C mount standard. This is because the optical path length (optical distance) of light focused on each imaging element depends on the refractive index of an optical system (for example, the branching optical system 400) disposed in the path of the light and the length of the path of the light guided through the optical system.

By increasing the refractive index of the branching optical system 400 as described above, it is possible to form the branching optical system 400 with a larger glass thickness while satisfying the flange back length conditions. Therefore, in accordance with the imaging apparatus 105b according to Example 1, it is possible to avoid physical interference between the first to fourth imaging elements 231 to 234 (eventually, the substrates 221 to 224) and to further improve the degree of freedom in the arrangement of each imaging element.

Further, as described above, the imaging apparatus 105b according to Example 1 realizes a relatively large F number. Therefore, in accordance with the imaging apparatus 105b according to Example 1, various optical systems from an optical system with a relatively large F number, such as a surgical microscope, to an optical system with a relatively small F number, such as an endoscope, can be widely used.

Up to now, an example of the more detailed configuration of the imaging apparatus 105b shown in FIGS. 4 and 5 has been described as Example 1.

EXAMPLE 2

Subsequently, another example of the more detailed configuration of the imaging apparatus according to the present embodiment will be described as Example 2. By increasing the refractive index of the branching optical system 400 as described above, it is possible to form the branching optical system 400 with a larger glass thickness while satisfying the flange back length conditions defined by a predetermined mount standard. Therefore, in Example 2, an example of a case will be described in which a glass material having a refractive index higher than that of the glass material applied in Example 1 is applied as a glass material forming each of prisms (that is, the first to fifth prisms 411 to 415) configuring the branching optical system 400.

Figure 10:
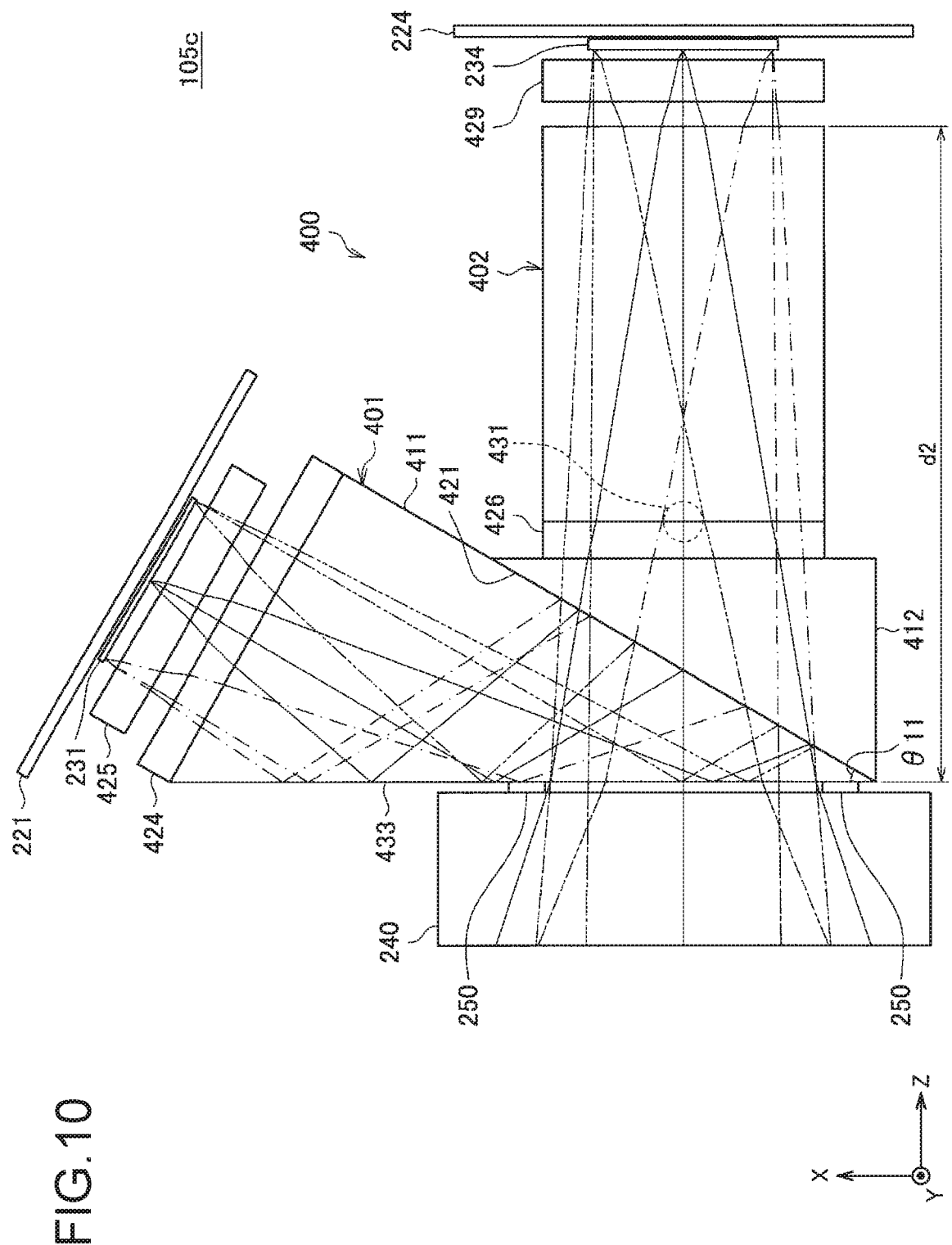
FIG. 10 is an explanatory diagram for describing an example of the configuration of an imaging apparatus according to Example 2.

For example, FIGS. 10 and 11 are explanatory diagrams for describing an example of the configuration of the imaging apparatus according to Example 2 of the present embodiment, and show another example of an imaging apparatus that can be applied as the camera head 105 of the endoscopic surgery system 100 described above. Note that, in the following description, the imaging apparatus according to Example 2 may be referred to as an "imaging apparatus 105c" in order to explicitly distinguish the imaging apparatus from other imaging apparatuses applicable as the camera head 105.

The imaging apparatus 105c according to Example 2 is different from the imaging apparatus 105b according to Example 1 described above in a glass material forming the first to fifth prisms 411 to 415. Therefore, in the imaging apparatus 105c according to Example 2, the dimensions of the first to fifth prisms 411 to 415 are different from those in the imaging apparatus 105b according to Example 1 due to the difference in the glass material. On the other hand, the other configurations of the imaging apparatus 105c according to Example 2 are the same as those of the imaging apparatus 105b according to Example 1.

Therefore, in this description, the imaging apparatus 105c according to Example 2 will be described focusing on portions different from the imaging apparatus 105b according to Example 1 described above, and detailed descriptions of portion substantially the same as those of the imaging apparatus 105b will be omitted. Note that, in FIGS. 10 and 11, it is assumed that configurations denoted by the same reference numerals as in FIGS. 4 and 5 show substantially the same configurations as in the example shown in FIGS. 4 and 5.

In the imaging apparatus 105c according to Example 2, a glass material satisfying the conditions of refractive index $Nd \geq 1.90$ is applied as a glass material forming the first to fifth prisms 411 to 415 configuring the branching optical system 400. As a specific example, a case will be described in which a glass material satisfying the conditions of refractive index $Nd=1.903658$ and Abbe number $vd=31.3150$ is used as a glass material forming the first to fifth prisms 411 to 415. Note that, as a glass material satisfying the same conditions, for example, TAFD25 manufactured by Hoya Co., Ltd. can be mentioned.

Further, in the imaging apparatus 105c according to Example 2, the size (that is, image height) of an image formed on each imaging element, the dimension and shape of an opening provided in the opening mask 250, and the F number at the center of the light receiving surface of each imaging element are the same as those in the imaging apparatus 105b according to Example 1 described with reference to FIGS. 3 and 4. Further, the angles of portions denoted by reference numerals θ11, θ13, and θ15 in FIGS. 10 and 11 are the same as the angles of portions denoted by the same reference numerals in FIGS. 4 and 5.

On the basis of the conditions described above, in the imaging apparatus 105c according to Example 2, the glass thickness d2 of the branching optical system 400 is 19.847 mm.

As described above, in the imaging apparatus 105c according to Example 2, a glass material having a refractive index higher than that in the example described as Example 1 is applied as a glass material forming the first to fifth prisms 411 to 415 configuring the branching optical system 400. As a result, in the imaging apparatus 105c according to Example 2, it is possible to form the branching optical system 400 with a larger glass thickness than that in the imaging apparatus 105b according to Example 1. That is, in accordance with the imaging apparatus 105c according to Example 2, it is possible to further improve the degree of freedom in the arrangement of the respective imaging elements (that is, the first to fourth imaging elements 231 to 234) compared with the imaging apparatus 105b according to Example 1.

Further, in accordance with the imaging apparatus 105c according to Example 2, it is possible to secure a larger clearance between the light and the side surface of the prism, the chamfered portion, and the apex of the prism, for example. Therefore, it is also possible to further reduce the risk of occurrence of flare due to these portions.

Note that, the dispersion tends to be larger (that is, the Abbe number tends to be smaller) as the refractive index of the glass material becomes higher. Further, such a glass material contains an oxide component having absorption in the near ultraviolet region in many cases. In such a case, the transmittance in the short wavelength region near 400 nm tends to be lower. In particular, in a prism optical system, the glass thickness tends to increase. In the imaging apparatus 105c according to this example, the glass pressure of the branching optical system 400 is 19.847 mm, and the influence due to a reduction in the transmittance may become apparent. In view of such a situation, particularly in a case where application to the medical field is assumed, it can be said that it is more desirable for achieving both color reproducibility and miniaturization of the optical system to apply a glass material, which satisfies the conditions of Abbe number $vd \geq 30.0$ in addition to the conditions of the refractive index described above, as a glass material forming each of prisms (that is, the first to fifth prisms 411 to 415) configuring the branching optical system 400.

Up to now, another example of the more detailed configuration of the imaging apparatus according to the present embodiment are described as Example 2 with reference to FIGS. 10 and 11.

Note that, the above-described Examples 1 and 2 are merely examples, and the glass material forming each prism of the branching optical system 400 is not necessarily limited to the examples described above as long as various conditions defined by a predetermined standard (for example, a C mount standard) and the conditions of color reproducibility according to the application can be satisfied. As a specific example, TAFD5F, TAFD30, TAFD33, TAFD37, TAFD35, TAFD45, and the like manufactured by Hoya Co., Ltd. can be mentioned as glass materials applicable as the branching optical system 400. On the other hand, the upper limit of each of the refractive index Nd and the Abbe number vd of each prism of the branching optical system 400 is substantially determined in accordance with the selection of a glass material applicable to each prism.

Further, the present disclosure is not limited to a case where the imaging apparatus according to the present embodiment is configured as an imaging apparatus based on the C mount standard described above. For example, the imaging apparatus according to the present embodiment can also be configured as an imaging apparatus based on another mount standard. Also in such a case, on the basis of various conditions (for example, a flange back length and the like) defined by corresponding standards, the dimension of each unit of the imaging apparatus according to the present embodiment (in particular, the dimension of each unit of the branching optical system 400) or the glass material forming each prism of the branching optical system 400 may be appropriately determined on the basis of the same design concept as above.

<3.3. Modification Examples of an Imaging Apparatus>

Figure 12:
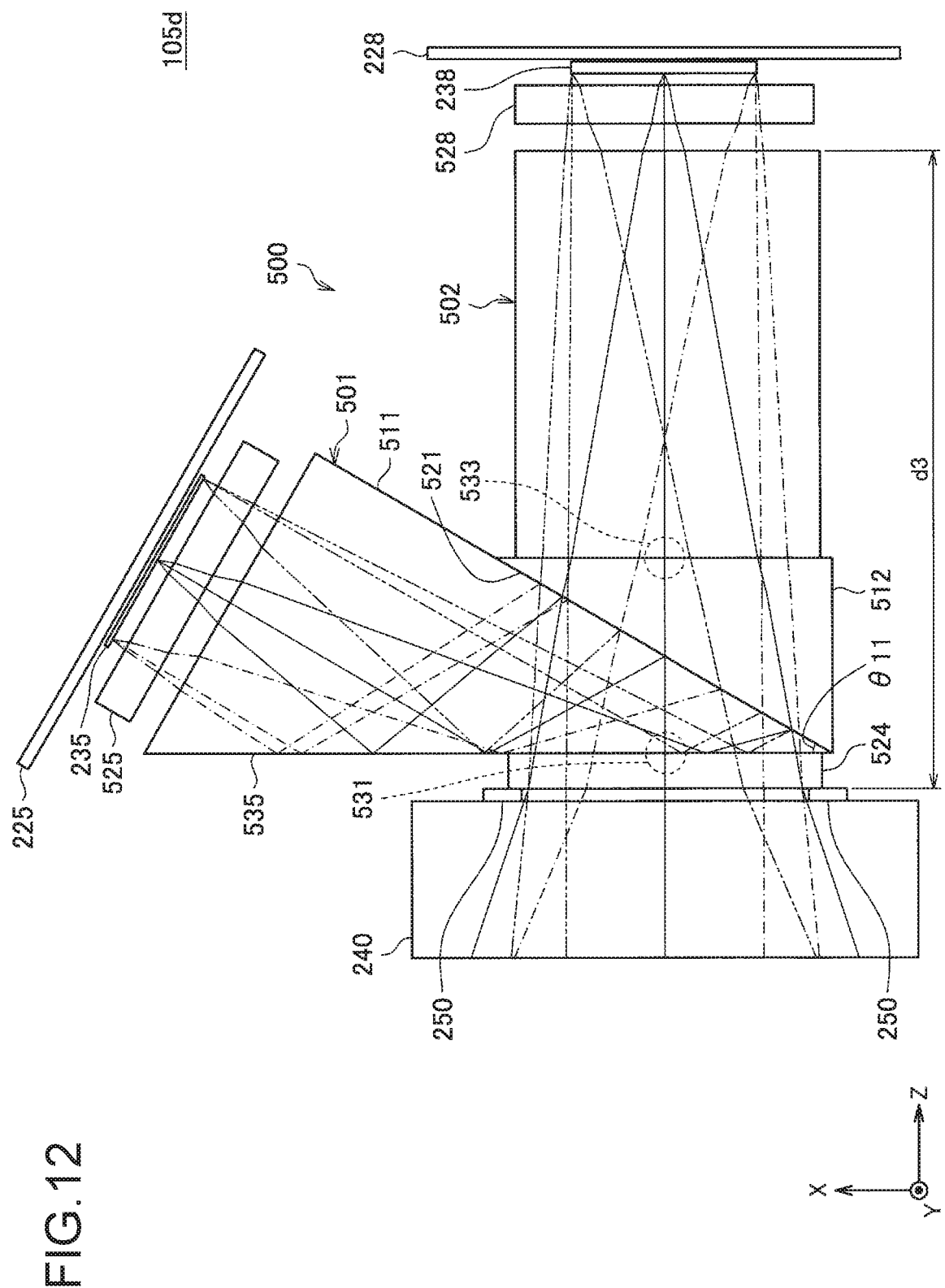
FIG. 12 is an explanatory diagram for describing an example of the configuration of an imaging apparatus according to a modification example.
Figure 13:
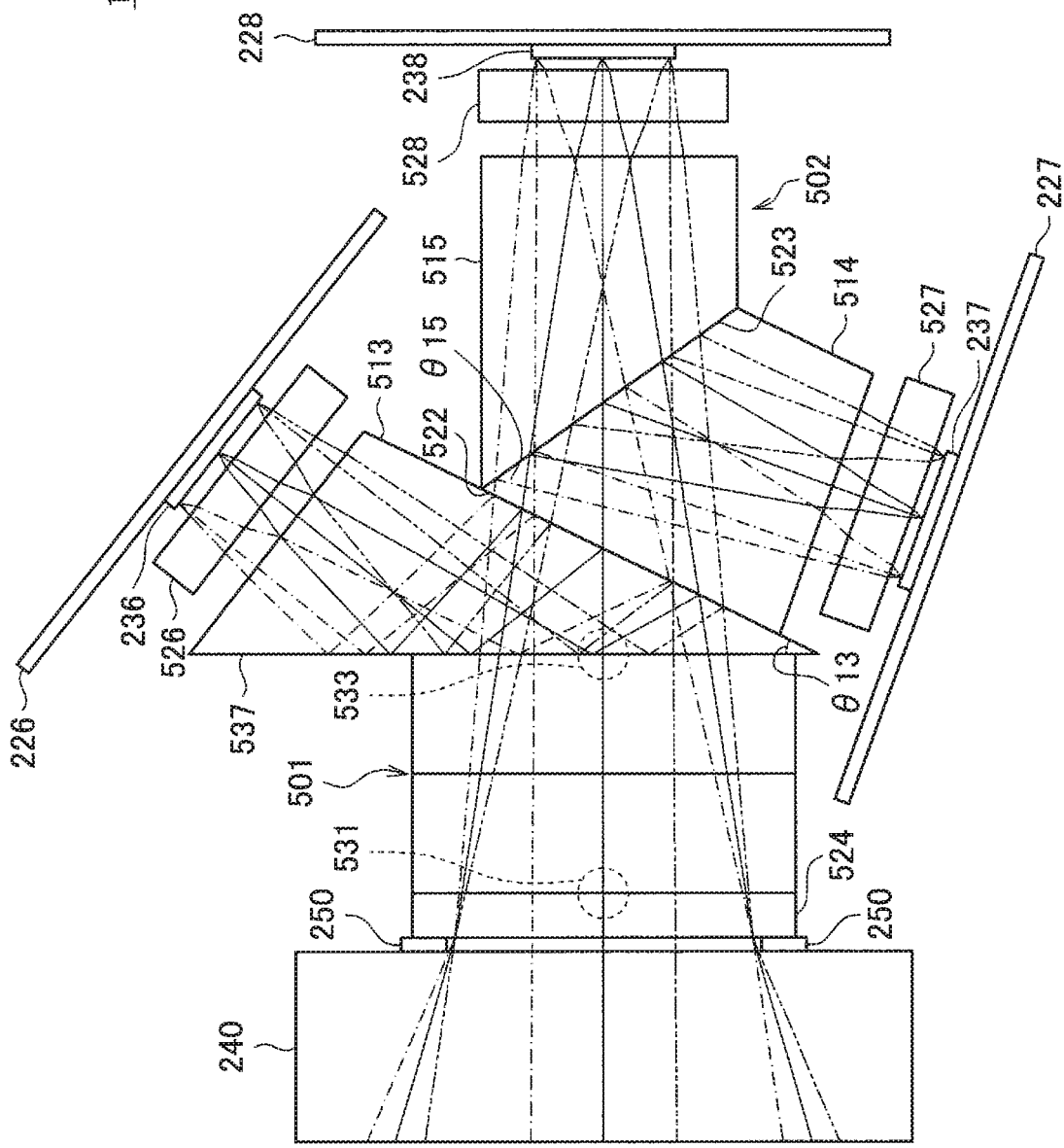
FIG. 13 is an explanatory diagram for describing an example of the configuration of an imaging apparatus according to a modification example.

Subsequently, as a modification example of the imaging apparatus according to the present embodiment, an example of the configuration of an imaging apparatus that separates light belonging to the visible light wavelength band into red light, green light, and blue light and focuses the respective light components after separation on four imaging elements will be described with reference to FIGS. 12 and 13. FIGS. 12 and 13 are explanatory diagrams for describing an example of the configuration of the imaging apparatus according to the modification example, and show another example of an imaging apparatus that can be applied as the camera head 105 of the endoscopic surgery system 100 described above. Further, in this description, it is assumed that the imaging apparatus according to the present embodiment is configured as an imaging apparatus based on the C mount standard. Note that, in the following description, the imaging apparatus shown in FIGS. 12 and 13 may be referred to as an "imaging apparatus 105*d*" in order to explicitly distinguish the imaging apparatus from other imaging apparatuses applicable as the camera head 105.

As shown in FIGS. 12 and 13, the imaging apparatus 105*d* according to the present embodiment includes a mount base 240, a branching optical system 500, first to fourth imaging elements 235 to 238, and substrates 225 to 228. The first to fourth imaging elements 235 to 238 are held by the substrates 225 to 228, respectively. Further, the imaging apparatus 105*d* may include an opening mask 250, or may include cover glasses 525 to 528. Note that, the configurations of the mount base 240 and the opening mask 250 are the same as those of the mount base 240 and the opening mask 250 in the imaging apparatus 105*b* according to the embodiment described above with reference to FIGS. 3 and 4. Therefore, in the following description, the configuration of the imaging apparatus 105*d* according to the modification example will be described focusing on portions different from the imaging apparatus 105*b* according to the embodiment described above, and detailed descriptions of portions substantially the same as those of the imaging apparatus 105*b* will be omitted.

Note that, in FIGS. 12 and 13, the z direction corresponds to the optical axis direction of light (that is, incident light) incident on the imaging apparatus 105*d*, in other words, the normal direction of the incidence surface of the branching optical system 500 that will be described in detail later. Further, it is assumed that both the x direction and the y direction are directions perpendicular to the z direction and the x direction and the y direction are perpendicular to each other. Note that, in FIGS. 12 and 13, the x direction corresponds to the horizontal direction of the imaging apparatus 105*d*, and the y direction corresponds to the vertical direction of the imaging apparatus 105*d*. Further, FIG. 12 schematically shows the configuration of the imaging apparatus 105*d* in a case where the imaging apparatus 105*d* is cut along a horizontal plane (xz plane) including the optical axis (z axis) of incident light, and also shows the optical path of light incident on the imaging apparatus 105*d*. That is, in FIG. 12, the horizontal direction, the vertical direction, and the depth direction of the diagram correspond to the z direction, the x direction, and the y direction, respectively. Further, FIG. 13 schematically shows the configuration of the imaging apparatus 105*d* in a case where the imaging apparatus 105*d* is cut along a vertical plane (yz plane) including the optical axis (z axis) of incident light, and also shows the optical path of light incident on the imaging apparatus 105*d*. That is, in FIG. 13, the horizontal direction, the vertical direction, and the depth direction of the diagram correspond to the z direction, the y direction, and the x direction, respectively.

As shown in FIGS. 12 and 13, the branching optical system 500 includes a first branching optical system 501, a second branching optical system 502, and an IR cut filter 524.

The first branching optical system 501 is a prism in which a first prism 511 and a second prism 512 are connected to each other with a dichroic film 521 interposed therebetween. That is, the dichroic film 521 is provided at the interface between the first prism 511 and the second prism 512. Further, the IR cut filter 524 is provided between the mount base 240 and the incidence surface 535 of the first prism 511. Note that, although not shown in detail in FIGS. 12 and 13, an air gap is provided at the interface between the IR cut filter 524 and the incidence surface 535 of the first prism 511 as indicated by reference numeral 531.

The IR cut filter 524 is a filter that cuts infrared light. As the IR cut filter 524, for example, the same one as the IR cut filter 426 described above with reference to FIG. 8 can be applied. That is, light belonging to the visible light wavelength band and light belonging to the near infrared wavelength band (that is, incident light), which are incident on the imaging apparatus 105*d* through the opening of the mount base 240, are incident on the first prism 511 from the incidence surface 534 after being transmitted through the IR cut filter 524. At this time, among the incident light components, the light belonging to the near infrared wavelength band is blocked by the IR cut filter 524, and the light belonging to the visible light wavelength band (that is, visible light) is incident on the first prism 511 from the incidence surface 535.

The first prism 511 is a prism on which light belonging to the visible light wavelength band is incident and which functions as an optical path for blue light through which the light belonging to the short wavelength side wavelength band including the B component is guided. Further, the second prism 512 is a prism that functions as an optical path for red light and green light through which the light belonging to the long wavelength side wavelength band including the R component and the G component, among the light components belonging to the visible light wavelength band, is guided.

The visible light incident on the first prism 511 from the incidence surface 535 travels straight through the first prism 511 and is separated into light belonging to the short wavelength side wavelength band including the B component and light belonging to the long wavelength side wavelength band including the R component and the G component by the dichroic film 521 provided obliquely on the optical axis.

Here, the light belonging to the short wavelength side wavelength band including the reflected and separated B component (hereinafter, also referred to as "blue light") reaches the incidence surface 535, as shown in FIG. 12. Further, as described above, an air gap is provided between the incidence surface 535 and the IR cut filter 524 as indicated by reference numeral 531. Therefore, the blue light is totally reflected only once at the incidence surface 535 and transmitted to the outside of the first prism 511. In this manner, the angle of the film forming surface of the dichroic film 521 with respect to the optical axis can be made to be approximately 90°. Conversely, the installation angle of the dichroic film 521 according to the present embodiment on the optical axis is set such that the total reflection conditions described above are satisfied. By arranging the dichroic film 521 in this manner, even in a case where light of a large F value is incident on the first prism 511, it is possible to suppress a change in the spectral characteristics of the dichroic film 521 due to the difference in incidence angle between left light and right light. Therefore, it is possible to perform wavelength separation with high accuracy.

The blue light transmitted through the first prism 511 is guided to the first imaging element 235. The first imaging element 235 is disposed such that the light receiving surface is perpendicular to the optical axis of the light (that is, blue light) transmitted through the first prism 511 and guided to the first imaging element 235. Note that, a cover glass 525 for protecting the light receiving surface of the first imaging element 235 may be interposed between the first prism 511 and the first imaging element 235. As the cover glass 525, for example, one using a glass material generally known as BK7 is applied. Further, as the first imaging element 235, for example, an imaging element in which no color filter is provided and which has high sensitivity for the wavelength band including the B component may be more desirably applied.

On the other hand, the light belonging to the long wavelength side wavelength band including the R component and the G component transmitted through the dichroic film 521 is incident on the second prism 512 and travels straight through the second prism 512. The end surface of the second prism 512 opposite to a side on which the dichroic film 421 is provided (in other words, the emission surface of the second prism 512 on the downstream side of the optical axis) is provided perpendicular to the optical axis. Therefore, the light belonging to the long wavelength side wavelength band guided through the second prism 512 is transmitted to the outside of the second prism 512 while maintaining a state in which the light belonging to the long wavelength side wavelength band guided through the second prism 512 is perpendicular to the emission surface of the second prism 512.

The second branching optical system 502 is connected to the emission surface of the second prism 512. Note that, although not shown in detail in FIGS. 12 and 13, an air gap is provided at the interface between the first branching optical system 501 and the second branching optical system 502 as indicated by reference numeral 533.

Subsequently, mainly with reference to FIG. 13, the configuration of each unit of the first branching optical system 501 located subsequent to the second prism 512 will be described. The light belonging to the long wavelength side wavelength band including the R component and the G component emitted from the second prism 512 of the first branching optical system 501 is incident on the second branching optical system 502.

The second branching optical system 502 separates the light belonging to the long wavelength side wavelength band including the R component and the G component incident on the second branching optical system 502 into light belonging to the wavelength band including the R component and light belonging to the wavelength band including the G component. Specifically, the second branching optical system 502 is a prism in which a third prism 513 and a fourth prism 514 are connected to each other with a dichroic film 522 interposed therebetween and the fourth prism 514 and a fifth prism 515 are connected to each other with a half mirror film 523 interposed therebetween. That is, the dichroic film 522 is provided at the interface between the third prism 513 and the fourth prism 514, and the half mirror film 523 is provided at the interface between the fourth prism 514 and the fifth prism 515.

The dichroic film 522 is an optical film that separates incident light, which is incident on the second branching optical system 502 and includes light belonging to the long wavelength side wavelength band including the R component and the G component, into light belonging to a wavelength band including the R component and light belonging to a wavelength band including the G component. Specifically, the dichroic film 522 has a characteristic of reflecting the light belonging to the wavelength band including the R component and transmitting the light belonging to the wavelength band including the G component.

Further, the half mirror film 523 is an optical film that branches the optical path of incident light, which includes light belonging to the wavelength band including the G component transmitted through the dichroic film 522, into two optical paths.

Specifically, the half mirror film 523 has a characteristic of reflecting some of the incident light and transmitting the other some.

The third prism 513 is a prism on which light belonging to the long wavelength side wavelength band including the R component and the G component is incident and which functions as an optical path for red light through which the light belonging to the wavelength band including the R component is guided. Further, the fourth prism 514 is a prism on which light belonging to the wavelength band including the G component is incident and which functions as a first optical path for green light through which some of the light belonging to the wavelength band including the G component is guided. Further, the fifth prism 515 is a prism that functions as a second optical path for green light through which the other some of the light belonging to the wavelength band including the G component is guided.

The light belonging to the long wavelength side wavelength band including the R component and the G component incident on the third prism 513 from an incidence surface 537 travels straight through the third prism 513 and is separated into light (that is, red light) belonging to the wavelength band including the R component and light (that is, green light) belonging to the wavelength band including the G component by the dichroic film 522 provided obliquely on the optical axis.

The red light is reflected by the dichroic film 522 and guided through the third prism 513. At this time, the dichroic film 522 reflects the red light in a direction twisted relative to a direction, in which the dichroic film 521 described above reflects the blue light, with the optical axis (that is, the z axis) of the incident light to the branching optical system 500 as its axis. That is, as shown in FIG. 12, in a case where the dichroic film 521 reflects the blue light in the surface direction of the xz plane, the dichroic film 522 reflects the red light in a direction crossing the xz plane. As a specific example, in the example shown in FIG. 13, the dichroic film 522 reflects the red light in the surface direction of a horizontal plane (that is, the yz plane where the xz plane and the normal direction are perpendicular to each other) including the z direction. In other words, in the example shown in FIG. 13, the dichroic film 522 reflects the red light in a direction approximately perpendicular to each of the optical axis of the incident light to the branching optical system 500 and a direction in which the dichroic film 521 reflects the blue light.

Here, the reflected and separated red light reaches the incidence surface 537, as shown in FIG. 13. Further, as described above, an air gap is provided between the incidence surface 537 and the emission surface of the second prism 512 as indicated by reference numeral 533. Therefore, the red light is totally reflected only once at the incidence surface 537 and transmitted to the outside of the third prism 513. In this manner, the angle of the film forming surface of the dichroic film 522 with respect to the optical axis can be made to be approximately 90°. Conversely, the installation angle of the dichroic film 522 according to the present embodiment on the optical axis is set such that the total reflection conditions described above are satisfied. By arranging the dichroic film 522 in this manner, even in a case where light of a large F value is incident on the third prism 513, it is possible to suppress a change in the spectral characteristics of the dichroic film 522 due to the difference in incidence angle between upper light and lower light. Therefore, it is possible to perform wavelength separation with high accuracy.

The red light transmitted through the third prism 513 is guided to the second imaging element 236. The second imaging element 236 is disposed such that the light receiving surface is perpendicular to the optical axis of the light transmitted through the third prism 513 and guided to the second imaging element 236. Note that, a cover glass 526 for protecting the light receiving surface of the second imaging element 236 may be interposed between the third prism 513 and the second imaging element 236. As the cover glass 526, the same one as the cover glass 525 described above can be applied. Further, as the second imaging element 236, for example, an imaging element in which no color filter is provided and which has high sensitivity for the wavelength band including the R component may be more desirably applied.

On the other hand, the green light transmitted through the dichroic film 522 is incident on the fourth prism 514. Then, the green light incident on the fourth prism 514 travels straight through the fourth prism 514 and is separated into some light and some other light (that is, the optical path of the incident green light branches into two optical paths) by the half mirror film 523 provided obliquely on the optical axis.

Some of the green light is reflected by the half mirror film 523 and guided through the fourth prism 514. At this time, the half mirror film 523 reflects some of the green light in a direction twisted relative to a direction, in which the dichroic film 521 described above reflects the blue light, with the optical axis (that is, the z axis) of the incident light to the branching optical system 500 as its axis. That is, as shown in FIG. 12, in a case where the dichroic film 521 reflects the blue light in the surface direction of the xz plane, the half mirror film 523 reflects some of the green light in a direction crossing the xz plane. As a specific example, in the example shown in FIG. 13, the half mirror film 523 reflects some of the green light in the surface direction of a horizontal plane (that is, the yz plane where the xz plane and the normal direction are perpendicular to each other) including the z direction, the surface direction being a direction different from the direction in which the dichroic film 522 reflects the red light.

Some of the reflected and separated green light is guided through the fourth prism 514. Further, some of the green light transmitted through the fourth prism 514 is guided to the third imaging element 237. The third imaging element 237 is disposed such that the light receiving surface is perpendicular to the optical axis of the light transmitted through the fourth prism 514 and guided to the third imaging element 237. Note that, a cover glass 527 for protecting the light receiving surface of the third imaging element 237 may be interposed between the fourth prism 514 and the third imaging element 237. As the cover glass 527, the same one as the cover glass 525 described above can be applied. Further, as the third imaging element 237, for example, an imaging element in which no color filter is provided and which has high sensitivity for the wavelength band including the G component may be more desirably applied.

Further, the other some of the green light transmitted through the half mirror film 523 is incident on the fifth prism 515 and travels straight through the fifth prism 515. The end surface of the fifth prism 515 opposite to a side on which the half mirror film 523 is provided (in other words, the emission surface of the fifth prism 515 on the downstream side of the optical axis) is provided perpendicular to the optical axis. Therefore, the other some of the green light guided through the fifth prism 515 is transmitted to the outside of the fifth prism 415 while maintaining a state in which the other some of the green light guided through the fifth prism 515 is perpendicular to the emission surface of the fifth prism 515. Then, the other some of the green light transmitted through the fifth prism 515 is guided to the fourth imaging element 238. The fourth imaging element 238 is disposed such that the light receiving surface is perpendicular to the optical axis of the light transmitted through the fifth prism 515 and guided to the fourth imaging element 238. Note that, a cover glass 528 for protecting the light receiving surface of the fourth imaging element 238 may be interposed between the fifth prism 515 and the fourth imaging element 238. As the cover glass 528, the same one as the cover glass 525 described above can be applied. Further, as the fourth imaging element 238, for example, an imaging element in which no color filter is provided and which has high sensitivity for the wavelength band including the G component may be more desirably applied.

As described above, in the imaging apparatus 105d according to the modification example, the visible light included in the incident light is separated into red light, green light, and blue light, and the red light, the green light, and the blue light are focused on different imaging elements. Further, at this time, the imaging apparatus 105d separates some of the green light separated from the incident light and focuses the separated some and the other some of the light on different imaging elements. Then, the imaging apparatus 105d according to the modification example separately captures images based on the light components (that is, red light, green light, and blue light) focused on the respective imaging elements. With such a configuration, in the imaging apparatus 105d according to the modification example, since it is not necessary to provide a color filter in each imaging element, the light use efficiency is improved. Therefore, compared with an imaging apparatus in which a color separation optical system is not used, it is possible to capture an image with further improved color reproducibility or resolution.

Further, the imaging apparatus 105d according to the modification example may be configured such that some of imaging elements, on which light components obtained by separation of incident light are focused, are disposed at positions shifted by ½ pixel in both horizontal and vertical directions, in which pixels are arranged, relative to the other imaging elements with the optical axis as a reference. For example, FIG. 14 is an explanatory diagram for describing one aspect of the imaging apparatus 105d according to the modification example, and shows an example of the relative positional relationship between the third imaging element 237 and the fourth imaging element 238.

Figure 14:
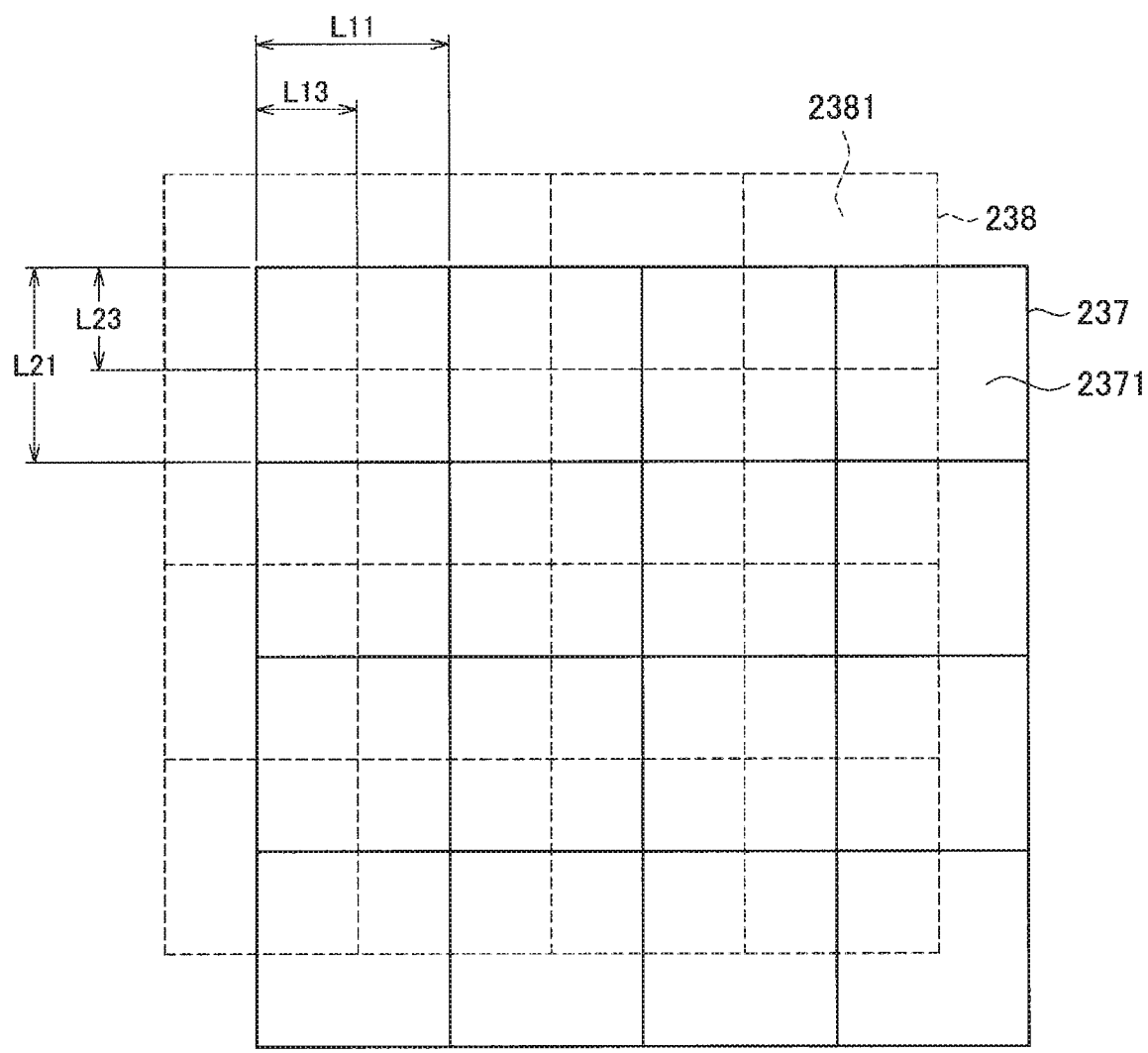
FIG. 14 is an explanatory diagram for describing an aspect of an imaging apparatus according to a modification example.

In FIG. 14, reference numeral 2371 indicates one pixel of the third imaging element 237. Further, reference numeral 2381 indicates one pixel of the fourth imaging element 238. Further, reference numeral L11 indicates the width of the pixel 2371 of the third imaging element 237 in the horizontal direction, and reference numeral L21 indicates the width of the pixel 2371 in the vertical direction. Further, a width L13 corresponds to ½ of the width L11, that is, corresponds to the distance of ½ pixel in the horizontal direction of the pixel 2371. Similarly, a width L23 corresponds to ½ of the width L21, that is, corresponds to the distance of ½ pixel in the vertical direction of the pixel 2371. Further, it is assumed that the pixel 2371 and the pixel 2381 have the same size in the vertical and horizontal directions.

As shown in FIG. 14, the fourth imaging element 238 is disposed at a position shifted by ½ pixel in both the horizontal and vertical directions, in which the pixels 2381 are arranged, relative to the third imaging element 237 with the optical axis of light focused on the third imaging element 237 and the fourth imaging element 238 as a reference. That is, each pixel 2381 of the fourth imaging element 238 is located between positions, at which the pixels 2371 of the third imaging element 237 are disposed, relatively in both the horizontal and vertical directions in which the pixels 2371 of the third imaging element 237 are disposed. On the basis of such a configuration, a captured image may be generated by combining the imaging results of the third imaging element 237 and the fourth imaging element 238 such that the optical axes of light components respectively focused on the third imaging element 237 and the fourth imaging element 238 approximately match each other, for example. With the above-described configuration, it is possible to interpolate information between pixels in the other imaging element from the imaging result of one imaging element. Therefore, it is possible to further improve the resolution of a captured image to be generated, compared with a captured image based on the imaging result of one imaging element.

In general, it is known that the human eye tends to strongly feel the resolution of light belonging to the G component among the R component, the G component, and the B component. Therefore, for example, by further improving the resolution of an image based on the imaging result of green light on the basis of the configuration described with reference to FIG. 14, an image with a higher resolution can be presented to the user as a visible light image based on the imaging results of the first to fourth imaging elements 235 to 238.

Up to now, as a modification example of the imaging apparatus according to the present embodiment, an example of the configuration of an imaging apparatus that separates light belonging to the visible light wavelength band into red light, green light, and blue light and focuses the respective light components after separation on four imaging elements has been described with reference to FIGS. 12 and 13.

EXAMPLE 3

Subsequently, as Example 3, an example of a more detailed configuration of the imaging apparatus 105d described with reference to FIGS. 12 and 13 will be described. Note that, in this example, an example of a case will be described in which the imaging apparatus 105d according to the modification example is configured as an imaging apparatus based on the C mount standard. That is, in Example 3, in order to satisfy the flange back length conditions (17.526 mm) defined by the C mount standard, an example of the configuration of the imaging apparatus 105b will be described in which the optical distance from at least the incidence surface of the branching optical system 500 to the imaging element located subsequent to the branching optical system 500 is 17.526 mm or less.

As a glass material forming the first to fifth prisms 511 to 515 configuring the branching optical system 500, a glass material satisfying the conditions of refractive index Nd=1.834805 and Abbe number vd=42.7218 is assumed to be used. Note that, as a glass material satisfying the same conditions, for example, TAFD5F manufactured by Hoya Co., Ltd. can be mentioned.

Further, as the cover glasses 525 to 528, for example, those having a thickness of 1.2 mm using BK7 as a glass material are used. Further, the IR cut filter 524 has a thickness of 1.09 mm in the optical axis direction.

Note that, in the imaging apparatus 105d according to Example 3, the size (that is, image height) of an image formed on each imaging element, the dimension and shape of an opening provided in the opening mask 250, and the F number at the center of the light receiving surface of each imaging element are the same as those in the imaging apparatus 105b according to Example 1 described with reference to FIGS. 3 and 4. Further, the angles of portions denoted by reference numerals θ11, θ13, and θ15 in FIGS. 12 and 13 are the same as the angles of portions denoted by the same reference numerals in FIGS. 4 and 5.

On the basis of the conditions described above, in the imaging apparatus 105d according to Example 3, the glass thickness d3 of the branching optical system 500 is 18.060 mm. As described above, also in the imaging apparatus 105d according to Example 3, it is possible to form the branching optical system 500 with a larger glass thickness while satisfying the flange back length conditions. Therefore, in accordance with the imaging apparatus 105d according to Example 3, it is possible to avoid physical interference between the first to fourth imaging elements 235 to 238 (eventually, the substrates 225 to 228) and to further improve the degree of freedom in the arrangement of each imaging element.

Further, the imaging apparatus 105*d* according to Example 3 realizes a relatively large F number. Therefore, in accordance with the imaging apparatus 105*d* according to Example 3, various optical systems from an optical system with a relatively large F number, such as a surgical microscope, to an optical system with a relatively small F number, such as an endoscope, can be widely used.

Note that, the above-described Example 3 is merely an example, and the glass material forming each prism of the branching optical system 500 is not necessarily limited to the examples described above as long as various conditions defined by a predetermined standard (for example, a C mount standard) and the conditions of color reproducibility according to the application can be satisfied. As a specific example, TAFD5F, TAFD30, TAFD33, TAFD37, TAFD35, TAFD45, and the like manufactured by Hoya Co., Ltd. can be mentioned as glass materials applicable as the branching optical system 500. On the other hand, the upper limit of each of the refractive index Nd and the Abbe number vd of each prism of the branching optical system 500 is substantially determined in accordance with a glass material applicable to each prism.

Up to now, an example of the more detailed configuration of the imaging apparatus 105*d* shown in FIGS. 12 and 13 has been described as Example 3.

<<4. Examples of Hardware Configuration>>

Figure 15:
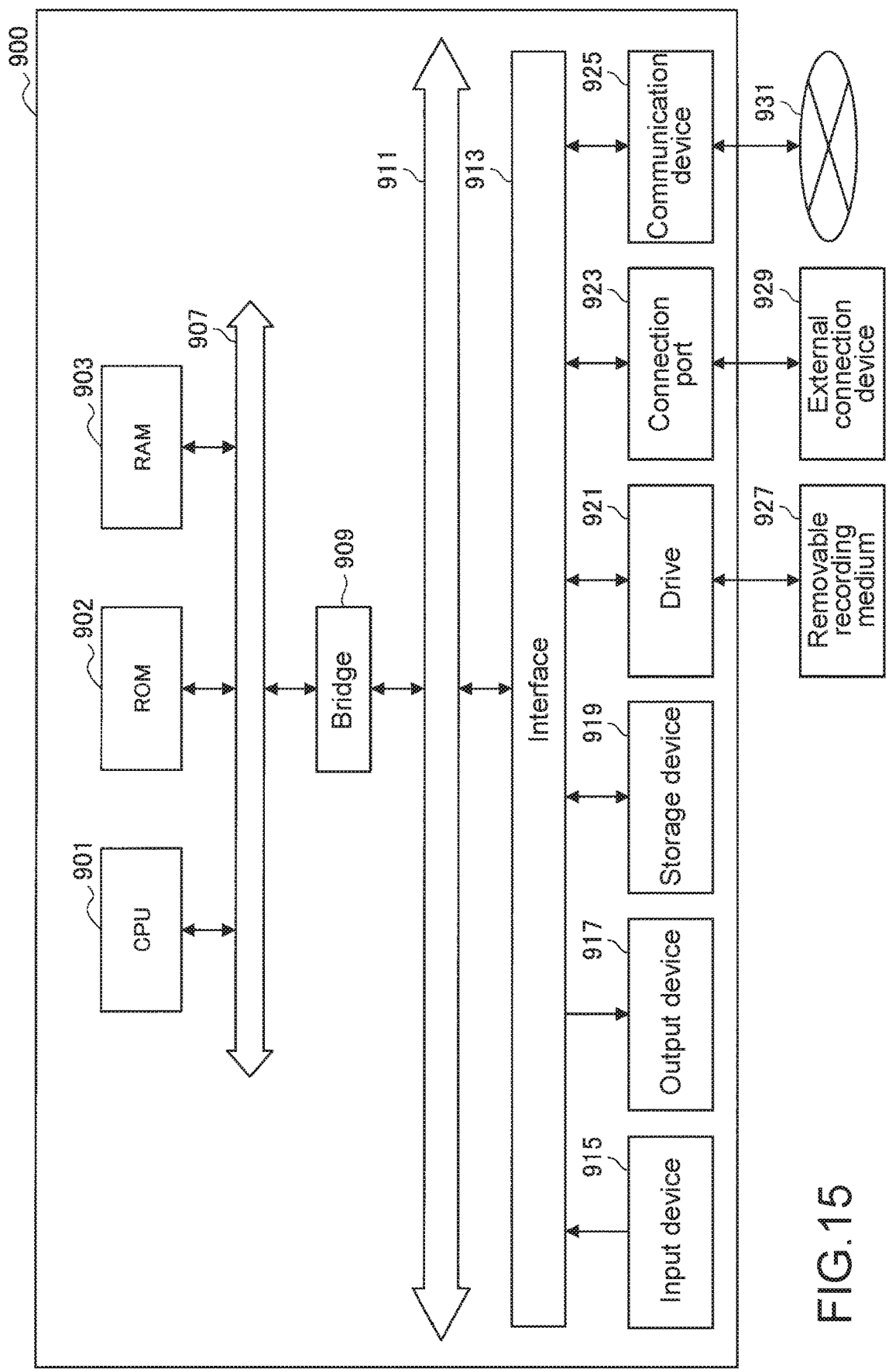
FIG. 15 is a functional block diagram showing one configuration example of the hardware configuration of an information processing apparatus that configures an endoscopic imaging system according to an embodiment of the present disclosure.

Subsequently, an example of the hardware configuration of a so-called information processing apparatus for executing various kinds of processing, such as the CCU in the endoscopic imaging system (that is, the endoscopic surgery system), will be described in detail with reference to FIG. 15. FIG. 15 is a functional block diagram showing one configuration example of the hardware configuration of an information processing apparatus that configures an endoscopic imaging system according to an embodiment of the present disclosure.

An information processing apparatus 900 configuring the endoscopic imaging system according to the present embodiment mainly includes a CPU 901, a ROM 903, and a RAM 905. Further, the information processing apparatus 900 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing unit and a control unit, and controls the entire operation or a part of the information processing apparatus 900 in accordance with various programs recorded in the ROM 903, the RAM 905, the storage device 919, or a removable recording medium 927. The ROM 903 stores programs, calculation parameters, and the like used by the CPU 901. The RAM 905 primarily stores programs used by the CPU 901, parameters that change appropriately in execution of the programs, and the like. These are connected to each other by the host bus 907 configured by an internal bus, such as a CPU bus.

The host bus 907 is connected to the external bus 911, such as a peripheral component interconnect/interface (PCI) bus, through the bridge 909. Further, the input device 915, the output device 917, the storage device 919, the drive 921, the connection port 923, and the communication device 925 are connected to the external bus 911 through the interface 913.

The input device 915 is an operation means operated by the user, such as a mouse, a keyboard, a touch panel, a button, a switch, a lever, and a pedal, for example. Further, the input device 915 may be, for example, a remote control means (so-called remote control) using infrared rays or other radio waves or the external connection device 929 such as a mobile phone or a PDA corresponding to the operation of the information processing apparatus 900. Furthermore, the input device 915 is configured to include, for example, an input control circuit that generates an input signal on the basis of information, which is input by the user using the above-described operation means, and outputs the generated input signal to the CPU 901. By operating the input device 915, the user of the information processing apparatus 900 can input various kinds of data to the information processing apparatus 900 or can give an instruction relevant to processing operations.

The output device 917 is a device capable of visually or aurally notifying the user of the acquired information. Such devices include display devices such as a CRT display device, a liquid crystal display device, a plasma display device, an EL display device, and a lamp, sound output devices such as a speaker and a headphone, printer apparatuses, and the like. The output device 917 outputs, for example, results obtained by various kinds of processing performed by the information processing apparatus 900. Specifically, the display device displays the results obtained by various kinds of processing performed by the information processing apparatus 900 as text or images. On the other hand, the sound output device converts an audio signal, such as reproduced sound data or sound data, into an analog signal and outputs the analog signal.

The storage device 919 is a data storage device configured as an example of a storage unit of the information processing apparatus 900. The storage device 919 is configured by, for example, a magnetic storage unit device such as a hard disk drive (HDD), a semiconductor storage device, an optical storage device, or a magneto-optical storage device. The storage device 919 stores programs executed by the CPU 901, various kinds of data, and the like.

The drive 921 is a reader and writer for recording media, and is built in or externally attached to the information processing apparatus 900. The drive 921 reads out information recorded on the removable recording medium 927, such as a mounted magnetic disk, an optical disk, a magneto-optical disk, or a semiconductor memory, and outputs the information to the RAM 905. Further, the drive 921 can also write a record on the removable recording medium 927, such as a mounted magnetic disk, an optical disk, a magneto-optical disk, or a semiconductor memory. The removable recording medium 927 is, for example, a DVD medium, an HD-DVD medium, or a Blu-ray (registered trademark) medium. Further, the removable recording medium 927 may be CompactFlash (CF) (registered trademark), a flash memory, or a secure digital memory card (SD memory card). Further, the removable recording medium 927 may be, for example, an integrated circuit card (IC card) in which a non-contact IC chip is mounted or an electronic device.

The connection port 923 is a port for direct connection to the information processing apparatus 900. Examples of the connection port 923 include a universal serial bus (USB) port, an IEEE1394 port, a small computer system interface (SCSI) port, and the like. Other examples of the connection port 923 include an RS-232C port, an optical audio terminal, a high-definition multimedia interface (HDMI) (registered trademark) port, and the like. By connecting the external connection device 929 to the connection port 923, the information processing apparatus 900 acquires various kinds of data directly from the external connection device 929, or provides various kinds of data to the external connection device 929.

The communication device 925 is, for example, a communication interface configured by a communication device or the like for connection to a communication network (network) 931. The communication device 925 is, for example, a communication card for wired or wireless local area network (LAN), Bluetooth (registered trademark), or wireless USB (WUSB). Further, the communication device 925 may be a router for optical communication, a router for asymmetric digital subscriber line (ADSL), a modem for various communications, or the like. The communication device 925 can transmit and receive signals and the like to and from the Internet and other communication devices in accordance with a predetermined protocol, such as TCP/IP, for example. Further, the communication network 931 connected to the communication device 925 may be configured by a network or the like connected by wire or wirelessly and may be, for example, the Internet, a home LAN, infrared communication, radio wave communication, or satellite communication.

Up to now, an example of the hardware configuration that can realize the function of the information processing apparatus 900 configuring the endoscopic imaging system according to the embodiment of the present disclosure has been shown. Each of the components described above may be configured using a general-purpose member, or may be configured by hardware specialized for the function of each component. Therefore, the hardware configuration to be used can be appropriately changed in accordance with the technical level at the time of implementing the present embodiment. Note that, although not shown in FIG. 15, it is needless to say that various configurations corresponding to the information processing apparatus 900 configuring the endoscopic imaging system are provided.

Note that, it is possible to create a computer program for realizing each function of the information processing apparatus 900, which configures the endoscopic imaging system according to the present embodiment described above, and to install the computer program on a personal computer or the like. Further, it is also possible to provide a computer-readable recording medium in which such a computer program is stored. Examples of the recording medium are a magnetic disk, an optical disk, a magneto-optical disk, a flash memory, and the like. Further, the computer program described above may be distributed through, for example, a network without using a recording medium. Further, the number of computers that execute the computer program is not particularly limited. For example, a plurality of computers (for example, a plurality of servers and the like) may be made to execute the computer program in cooperation with each other.

<<5. Application examples>>

Subsequently, as an application example of an imaging system according to an embodiment of the present disclosure, an example of a case where the imaging system is configured as a microscope imaging system including a microscope unit will be described with reference to FIG. 16.

Figure 16:
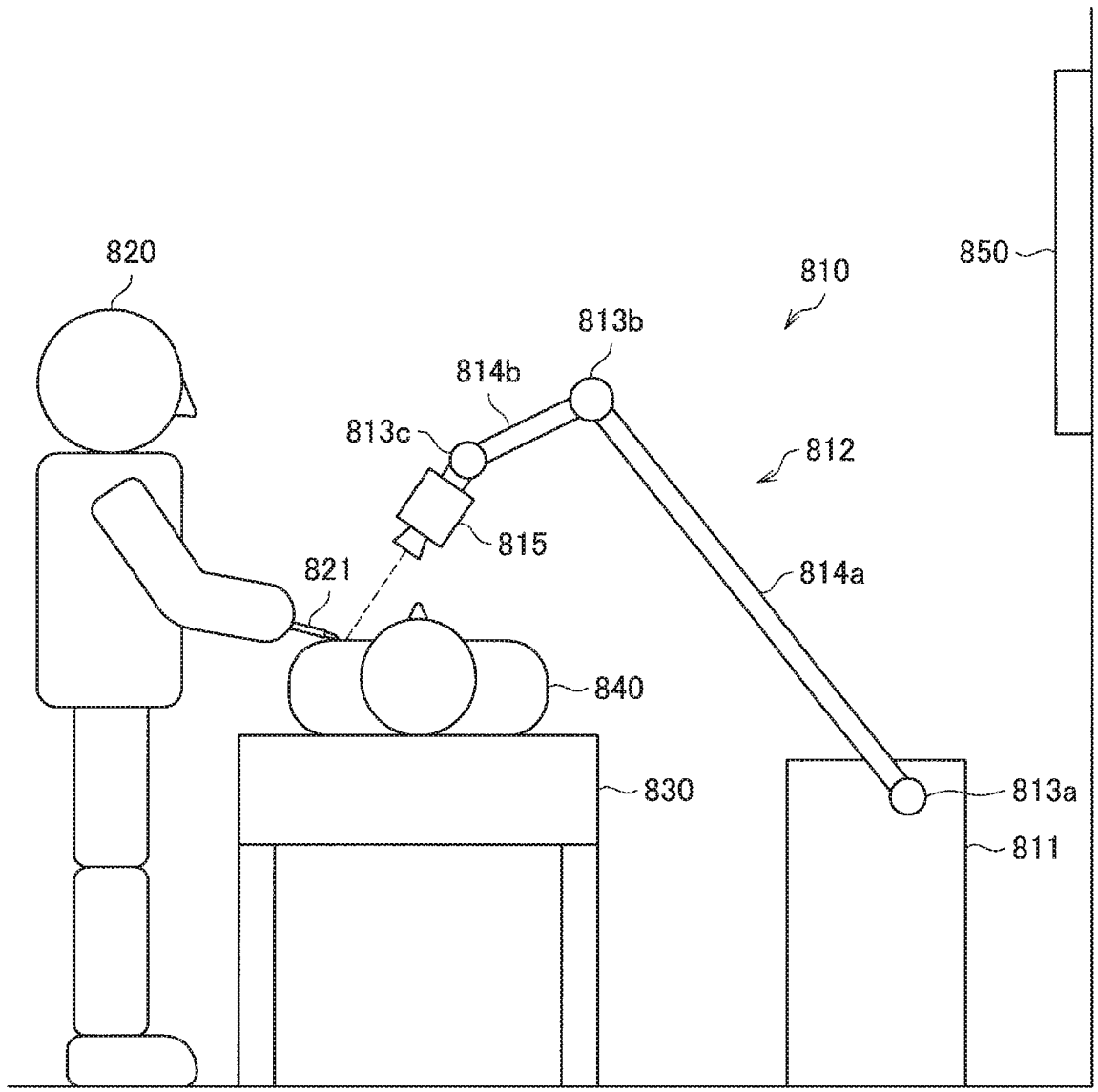
FIG. 16 is an explanatory diagram for describing an application example of an imaging system according to an embodiment of the present disclosure.

FIG. 16 is an explanatory diagram for describing an application example of an imaging system according to an embodiment of the present disclosure, and shows an example of the schematic configuration of a microscope imaging system. Specifically, FIG. 16 shows, as an application example in which the microscope imaging system according to an embodiment of the present disclosure is used, an example in which a surgical video microscope apparatus including an arm is used.

For example, FIG. 16 schematically shows how treatment using a surgical video microscope apparatus is performed. Specifically, referring to FIG. 16, a situation is illustrated in which a doctor, who is a person performing treatment (user) 820, performs surgery on a treatment target (patient) 840 on a treatment table 830 using a surgical tool 821, such as a scalpel and forceps, for example. Note that, in the following description, it is assumed that the treatment is a generic term for various medical treatments, such as surgery or examinations, performed on a patient who is the treatment target 840 by a doctor who is the user 820. Further, although the situation of surgery is illustrated as an example of the treatment in the example shown in FIG. 16, the treatment for which a surgical video microscope apparatus 810 is used is not limited to surgery but may be various other treatments.

The surgical video microscope apparatus 810 is provided beside the treatment table 830. The surgical video microscope apparatus 810 includes a base unit 811 that is a pedestal, an arm unit 812 extending from the base unit 811, and an imaging unit 815 that is connected to the distal end of the arm unit 812 as a distal end unit. The arm unit 812 has a plurality of joint portions 813a, 813b, and 813c, a plurality of links 814a and 814b connected to each other by the joint portions 813a and 813b, and the imaging unit 815 provided at the distal end of the arm unit 812. In the example shown in FIG. 16, for the sake of convenience, the arm unit 812 has the three joint portions 813a to 813c and the two links 814a and 814b. In practice, however, in consideration of the degree of freedom of the positions and postures of the arm unit 812 and the imaging unit 815, the numbers or the shapes of the joint portions 813a to 813c and the links 814a and 814b, directions of the driving axes of the joint portions 813a to 813c, and the like may be appropriately set so as to realize the desired degree of freedom.

The joint portions 813a to 813c have a function of rotatably connecting the links 814a and 814b to each other, and the driving of the arm unit 812 is controlled by driving the rotation of the joint portions 813a to 813c. Here, in the following description, the position of each component of the surgical video microscope apparatus 810 means a position (coordinates) in a space defined for driving control, and the posture of each component means a direction (angle) with respect to an arbitrary axis in the space defined for driving control. Further, in the following description, the driving (or driving control) of the arm unit 812 means driving (or driving control) of the joint portions 813a to 813c and means that the position and posture of each component of the arm unit 812 are changed (this change is controlled) by performing the driving (or driving control) of the joint portions 813a to 813c.

The imaging unit 815 is connected to the distal end of the arm unit 812 as a distal end unit. The imaging unit 815 is a unit that acquires an image of an imaging target. For example, the imaging unit 815 is a camera that can capture a moving image or a still image. As shown in FIG. 16, the postures or positions of the arm unit 812 and the imaging unit 815 are controlled by the surgical video microscope apparatus 810 so that the imaging unit 815 provided at the distal end of the arm unit 812 captures an image of a treatment part of the treatment target 840. Note that, the configuration of the imaging unit 815 connected to the distal end of the arm unit 812 as a distal end unit is not particularly limited. For example, the imaging unit 815 is configured as a microscope that acquires an enlarged image of an imaging target. Further, the imaging unit 815 may be configured so as to be attachable to and detachable from the arm unit 812. With such a configuration, for example, the imaging unit 815 corresponding to the purpose may be appropriately connected to the distal end of the arm unit 812 as a distal end unit. Note that, as the imaging unit 815, for example, an imaging apparatus to which the branching optical system according to the above-described embodiment is applied can be applied. Further, although this description is focused on a case where the imaging unit 815 is applied as a distal end unit, the distal end unit connected to the distal end of the arm unit 812 is not necessarily limited to the imaging unit 815.

Further, a display device 850, such as a monitor or a display, is installed at a position facing the user 820. An image of a treatment part captured by the imaging unit 815 is displayed as an electronic image on the display screen of the display device 850. The user 820 performs various kinds of treatments while viewing the electronic image of the treatment part displayed on the display screen of the display device 850.

With the above-described configuration, it is possible to perform surgery while imaging the treatment part with the surgical video microscope apparatus 810.

<<6. Conclusion>>

As described above, the branching optical system applied to the imaging apparatus according to the present embodiment includes the first branching optical system and the second branching optical system. The first branching optical system separates the first light belonging to a predetermined wavelength band from incident light in the first direction that is the surface direction of a plane including an optical axis corresponding to the normal direction of the incidence surface on which the incident light is incident. Further, the second branching optical system is provided subsequent to the first branching optical system, and separates, from the second light after the first light is separated from the incident light, the third light that is a part of the second light, in the second direction crossing the above-described plane.

With the above-described configuration, in the imaging apparatus according to the present embodiment, a plurality of imaging elements on which light components separated by the above-described branching optical system is focused (eventually, respective substrates that support the plurality of imaging elements) can be efficiently disposed in a limited space. Therefore, for example, in accordance with the imaging apparatus according to the present embodiment, it is possible to avoid physical interference between a plurality of imaging elements (eventually, physical interference between substrates that support the respective imaging elements).

Further, in a case where the imaging apparatus according to the present embodiment is configured as an imaging apparatus based on the C mount standard in consideration of use in the medical field, it is desirable that the first branching optical system and the second branching optical system configuring the above-described branching optical system satisfy the conditions of refractive index Nd≥1.80. Further, in this case, it is more desirable that the first branching optical system and the second branching optical system satisfy the conditions of refractive index Nd≥1.90 and Abbe number vd≥30. By adopting such a configuration, it is possible to miniaturize the optical system so as to satisfy the conditions of color reproducibility required in the medical field and to satisfy various conditions defined by the C mount standard.

While the desirable embodiments of the present disclosure have been described in detail with reference to the accompanying diagrams, the technical scope of the present disclosure is not limited to such examples. It is apparent to those skilled in the art of the present disclosure that various changes or modifications can be made within the scope of the technical idea described in the claims, and it is naturally understood that these also fall within the technical scope of the present disclosure.

Further, the effects described in this specification are merely illustrative or exemplary and not limitative. That is, the technology according to the present disclosure can exhibit other effects apparent to those skilled in the art from the description of this specification, in addition to or instead of the effects described above.

Note that, the following configurations are also within the technical scope of the present disclosure.

(1) A branching optical system including: a first branching optical system that separates first light belonging to a predetermined wavelength band from incident light in a first direction that is a surface direction of a plane including an optical axis corresponding to a normal direction of an incidence surface on which the incident light is incident; and a second branching optical system that is provided subsequent to the first branching optical system and separates, from second light after the first light is separated from the incident light, third light that is a part of the second light, in a second direction crossing the plane.

(2) The branching optical system described in (1), in which the second branching optical system separates, from fourth light after the third light is separated from the second light, fifth light that is a part of the fourth light, in a third direction crossing the plane and different from the second direction.

(3) The branching optical system described in (2), in which each of the second direction and the third direction is a surface direction of a second plane whose normal direction is different from that of a first plane that is the plane.

(4) The branching optical system described in any one of (1) to (3), in which the second direction is a direction approximately perpendicular to each of the optical axis and the first direction.

(5) The branching optical system described in any one of (1) to (4), in which an air gap is provided between an emission surface of the first branching optical system, from which the second light is emitted, and an incidence surface of the second branching optical system.

(6) The branching optical system described in (5), in which, after being separated from the second light, the third light is reflected on an incidence surface of the second branching optical system and emitted to outside of the second branching optical system.

(7) The branching optical system described in any one of (1) to (6), which further includes a first filter that is disposed so as to be interposed between the first branching optical system and the second branching optical system and blocks light belonging to the predetermined wavelength band.

(8) The branching optical system described in any one of (1) to (6), which further includes a second filter that is disposed before the first branching optical system and blocks light belonging to a first wavelength band and in which the first light is light belonging to a second wavelength band different from the first wavelength band among light components transmitted through the second filter.

(9) The branching optical system described in any one of (1) to (8), in which the first branching optical system has a dichroic film that separates the first light from the incident light.

(10) The branching optical system described in any one of (1) to (9), in which the second branching optical system has a dichroic film that separates light belonging to another wavelength band, which is different from the predetermined wavelength band, from at least a part of the second light.

(11) The branching optical system described in any one of (1) to (10), in which second branching optical system has a half mirror that branches at least a part of an optical path of the second light into a plurality of optical paths.

(12) The branching optical system described in any one of (1) to (11), in which the first branching optical system and the second branching optical system satisfy conditions of refractive index Nd≥1.80.

(13) The branching optical system described in (12), in which the first branching optical system and the second branching optical system satisfy conditions of refractive index Nd≥1.90 and Abbe number vd≥30.0.

(14) An imaging apparatus including a first branching optical system that separates first light belonging to a predetermined wavelength band from incident light in a first direction that is a surface direction of a plane including an optical axis corresponding to a normal direction of an incidence surface on which the incident light is incident; a second branching optical system that is provided subsequent to the first branching optical system and separates, from second light after the first light is separated from the incident light, third light that is a part of the second light, in a second direction crossing the plane; a first imaging element which is provided subsequent to the first branching optical system and on which the first light is focused; a second imaging element which is provided subsequent to the second branching optical system and on which at least a part of the third light is focused; and a third imaging element which is provided subsequent to the second branching optical system and on which at least a part of fourth light after the third light is separated from the second light is focused.

(15) The imaging apparatus described in (14), in which some of a plurality of imaging elements on which a plurality of light components separated by the second branching optical system is focused are disposed at positions shifted by ½ pixel in both horizontal and vertical directions, in which pixels are arranged, relative to the other imaging elements of the plurality of imaging elements with the optical axis as a reference.

(16) The imaging apparatus described in (14) or (15), in which an optical distance between an incidence surface of the first branching optical system and at least one of the first to third imaging elements satisfies flange back length conditions defined by a predetermined mount standard.

(17) The imaging apparatus described in (16), in which the predetermined mount standard is a C mount and the optical distance is 17.526 mm or less.

(18) An imaging system which includes: an optical system unit; and an imaging apparatus that captures an image acquired by the optical system unit and in which the imaging apparatus includes: a first branching optical system that separates first light belonging to a predetermined wavelength band from incident light in a first direction that is a surface direction of a plane including an optical axis corresponding to a normal direction of an incidence surface on which the incident light is incident; a second branching optical system that is provided subsequent to the first branching optical system and separates, from second light after the first light is separated from the incident light, third light that is a part of the second light, in a second direction crossing the plane; a first imaging element which is provided subsequent to the first branching optical system and on which the first light is focused; a second imaging element which is provided subsequent to the second branching optical system and on which at least a part of the third light is focused; and a third imaging element which is provided subsequent to the second branching optical system and on which at least a part of fourth light after the third light is separated from the second light is focused.

(19) The imaging system described in (18), in which an endoscope unit including a lens barrel inserted into a body cavity of a subject is provided as the optical system unit.

(20) The imaging system described in (18), in which a microscope unit that acquires an enlarged image of an imaging target is provided as the optical system unit.

REFERENCE SIGNS LIST 100 endoscopic surgery system
105 camera head
221 to 228 substrate
231, 235 first imaging element
232, 236 second imaging element
233, 237 third imaging element
234, 238 fourth imaging element
240 mount base
250 opening mask
400 branching optical system
401, 501 first branching optical system
402, 502 second branching optical system
411, 511 first prism
412, 512 second prism
413, 513 third prism
414, 514 fourth prism
415, 515 fifth prism
421, 521 dichroic film
422, 522 dichroic film
423 dichroic film
424 band pass filter
425, 427 to 429, 525 to 528 cover glass
426 IR cut filter
434 band pass filter
523 half mirror film
524 IR cut filter

The invention claimed is:

1. A branching optical system, comprising:
a first branching optical system that separates first light belonging to a predetermined wavelength band from incident light in a first direction that is a surface direction of a plane including an optical axis corresponding to a normal direction of an incidence surface on which the incident light is incident; and
a second branching optical system that is provided subsequent to the first branching optical system and separates, from second light after the first light is separated from the incident light, third light that is a part of the second light, in a second direction crossing the plane, wherein
the first branching optical system and the second branching optical system satisfy conditions of refractive index Nd≥1.90 and Abbe number vd≥30.0.

2. The branching optical system according to claim 1, wherein
the second branching optical system separates, from fourth light after the third light is separated from the second light, fifth light that is a part of the fourth light, in a third direction crossing the plane and different from the second direction.

3. The branching optical system according to claim 2, wherein
each of the second direction and the third direction is a surface direction of a second plane whose normal direction is different from the normal direction of the plane.

4. The branching optical system according to claim 1, wherein
the second direction is a direction approximately perpendicular to each of the optical axis and the first direction.

5. The branching optical system according to claim 1, wherein
an air gap is provided between an emission surface of the first branching optical system, from which the second light is emitted, and an incidence surface of the second branching optical system.

6. The branching optical system according to claim 5, wherein
after being separated from the second light, the third light is reflected on an incidence surface of the second branching optical system and emitted to outside of the second branching optical system.

7. The branching optical system according to claim 1, further comprising:
a first filter that is disposed so as to be interposed between the first branching optical system and the second branching optical system and blocks light belonging to the predetermined wavelength band.

8. The branching optical system according to claim 1, further comprising:
a second filter that is disposed before the first branching optical system and blocks light belonging to a first wavelength band, wherein
the first light is light belonging to a second wavelength band different from the first wavelength band among light components transmitted through the second filter.

9. The branching optical system according to claim 1, wherein
the first branching optical system has a dichroic film that separates the first light from the incident light.

10. The branching optical system according to claim 1, wherein
the second branching optical system has a dichroic film that separates light belonging to another wavelength band, which is different from the predetermined wavelength band, from at least a part of the second light.

11. The branching optical system according to claim 1, wherein
the second branching optical system has a half mirror that branches at least a part of an optical path of the second light into a plurality of optical paths.

12. An imaging apparatus, comprising:
a first branching optical system that separates first light belonging to a predetermined wavelength band from incident light in a first direction that is a surface direction of a plane including an optical axis corresponding to a normal direction of an incidence surface on which the incident light is incident;
a second branching optical system that is provided subsequent to the first branching optical system and separates, from second light after the first light is separated from the incident light, third light that is a part of the second light, in a second direction crossing the plane;
a first imaging element which is provided subsequent to the first branching optical system and on which the first light is focused; and
a second imaging element which is provided subsequent to the second branching optical system and on which at least a part of the third light is focused, wherein
an optical distance between an incidence surface of the first branching optical system and at least one of the first and second imaging elements satisfies flange back length conditions defined by a predetermined mount standard.

13. The imaging apparatus according to claim 12, wherein
some of a plurality of imaging elements on which a plurality of light components separated by the second branching optical system is focused are disposed at positions shifted by ½ pixel in both horizontal and vertical directions, in which pixels are arranged, relative to the other imaging elements of the plurality of imaging elements with the optical axis as a reference.

14. The imaging apparatus according to claim 12, wherein
the predetermined mount standard is a C mount, and
the optical distance is 17.526 mm or less.

15. An imaging system, comprising:
an optical system; and
an imaging apparatus that captures an image acquired by the optical system, wherein
the imaging apparatus includes:
a first branching optical system that separates first light belonging to a predetermined wavelength band from incident light in a first direction that is a surface direction of a plane including an optical axis corresponding to a normal direction of an incidence surface on which the incident light is incident;
a second branching optical system that is provided subsequent to the first branching optical system and separates, from second light after the first light is separated from the incident light, third light that is a part of the second light, in a second direction crossing the plane;
a first imaging element which is provided subsequent to the first branching optical system and on which the first light is focused; and
a second imaging element which is provided subsequent to the second branching optical system and on which at least a part of the third light is focused, wherein
an optical distance between an incidence surface of the first branching optical system and at least one of the first and second imaging elements satisfies flange back length conditions defined by a predetermined mount standard.

16. The imaging system according to claim 15, wherein
an endoscope including a lens barrel inserted into a body cavity of a subject is provided as the optical system.

17. The imaging system according to claim 15, wherein
a microscope that acquires an enlarged image of an imaging target is provided as the optical system.

18. The imaging apparatus according to claim 12, further comprising:
a third imaging element which is provided subsequent to the second branching optical system and on which at least a part of fourth light after the third light is separated from the second light is focused.

19. The imaging system according to claim 15, wherein
the imaging apparatus further includes a third imaging element which is provided subsequent to the second branching optical system and on which at least a part of fourth light after the third light is separated from the second light is focused.

* * * * *